US006566541B2

(12) United States Patent
Liu et al.

(10) Patent No.: US 6,566,541 B2
(45) Date of Patent: May 20, 2003

(54) TYPE 2 METHIONINE AMINOPEPTIDASE (METAP2) INHIBITORS AND USES THEREOF

(75) Inventors: Jun O. Liu, Cambridge, MA (US); Eric C. Griffith, Somerville, MA (US); Zhuang Su, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/813,555

(22) Filed: Mar. 21, 2001

(65) Prior Publication Data

US 2001/0034455 A1 Oct. 25, 2001

Related U.S. Application Data

(62) Division of application No. 09/093,448, filed on Jun. 8, 1998, now Pat. No. 6,207,704.
(60) Provisional application No. 60/049,159, filed on Jun. 9, 1997.

(51) Int. Cl.[7] .................... C07D 303/08; C07D 303/14; C07D 303/18; C07D 303/36
(52) U.S. Cl. ........................ 549/551; 549/554; 549/555; 549/556; 549/558; 549/559; 549/560; 514/475
(58) Field of Search ................................ 549/551, 554, 549/555, 556, 558, 559, 560; 514/475

(56) References Cited

U.S. PATENT DOCUMENTS

| 5,096,892 A | 3/1992 | Folkman et al. ............... 514/56 |
| 5,135,919 A | 8/1992 | Folkman et al. ............... 514/56 |
| 5,135,920 A | 8/1992 | Kanamaru et al. ............. 514/59 |
| 5,164,410 A | 11/1992 | Kishimoto et al. .......... 514/475 |
| 5,166,172 A | 11/1992 | Kishimoto et al. .......... 514/475 |
| 5,180,735 A | 1/1993 | Kishimoto et al. .......... 514/443 |
| 5,180,738 A | 1/1993 | Kishimoto et al. .......... 514/475 |
| 5,196,406 A | 3/1993 | Kamei et al. ................... 514/58 |
| 5,204,345 A | 4/1993 | Kishimoto et al. ....... 514/231.5 |
| 5,290,807 A | 3/1994 | Folkman et al. ............. 514/475 |
| 5,328,930 A | 7/1994 | Wilson ........................ 514/475 |
| 5,504,074 A | 4/1996 | D'Amato et al. ............ 514/183 |
| 5,698,586 A | 12/1997 | Kishimoto et al. .......... 514/475 |
| 5,767,293 A | 6/1998 | Oku et al. .................... 549/332 |
| 5,789,405 A | 8/1998 | Oku et al. ................. 514/227.8 |
| 6,207,704 B1 | 3/2001 | Liu et al. ..................... 514/475 |

FOREIGN PATENT DOCUMENTS

| EP | 0 359 036 | 3/1990 |
| EP | 0 386 667 | 9/1990 |
| EP | 0 415 294 | 3/1991 |
| JP | 7-17957 | * 1/1995 |

OTHER PUBLICATIONS

Antoine et al., "AGM–1470, a Potent Angiogensis Inhibitor, Prevents the Entry of Normal But not Transformed Endothelial Cells into the G. Phase of the Cell Cycle", Cancer Res. 54:2073–2076, 1994.

Arfin et al., "Eukaryotic Methionyl Aminopeptidase: Two Classes of Cobalt–Dependent Enzymes", Proc. Natl. Acad. Sci. USA. 92:7714–7718, 1995.

Breier et al., "Expression of Vascular Endothelial Growth Factor During Embryonic Angiogenesis and Endothelial Cell Differentiation", Development, 114:521–532, 1992.

Chang et al., "Purification and Characterization of a Methionine Aminopeptidasse from Saccharomyces Cerevisiae", J. Biol. Chem., 265:19892–19897, 1990.

Chang et al., "Molecular Cloning, Sequencing, Deletion, and Overexpression of a Methionine Aminopeptidase Gene from Saccharomyces Cerevisiae", J. Biol. Chem., 267: 8007–8011, 1992.

Datta et al., "Roles of 67–k–Da Polypeptide in Reversal of Protein Synthesis Inhibition in Hem–Deficient Reticulocyte Lysate", Proc. Natl. Acad. Sci. USA, 85: 3324–3328, 1988.

Griffith et al., "Methionine Aminopeptidase (Type 2) is the Common Target for Angiogenesis Inhibitors AGM–1470 and Ovalicin", Chemistry & Biology, 4:461–471, 1997.

Griffith et al., "Molecular Recognition of Angiogenesis Inhibitors Fumagillin and Ovalicin by Methionine Aminopeptidase 2", Proc. Natl. Acad. Sci. USA, 95: 15183–15188, 1998.

Li and Chang, "Amino–Terminal Protein Processing in Saccharomyces Cerevisiae is an Essential Function that Requires Two Distince methionine Aminopeptidase", Proc. Natl. Acad. Sci., 92: 12357–12361, 1995.

Li and Chang, "Evidence That the Human Homologue of a Rat Initiation Factor: 2–Associated protein ($P^{67}$) Is a Methionine Aminopeptidase", Biochem. Biophys. Res. Commun,, 227:152–159, 1996.

Li and Chang, "Molecular Cloning of a Human Complementary DNA Encoding an Initiation Factor 2–Associated Protein ($P^{67}$)", Biochem. Biophys. Acta., 1260:333–336, 1995.

Marui et al., "Chemical Modification of Fumagillin, III. Modification of the Spiro–Epoxide", Chem. Pharm. Bull., 43:588–593, 1995.

(List continued on next page.)

Primary Examiner—Ba K. Trinh
(74) Attorney, Agent, or Firm—Choate, Hall & Stewart; Brenda Herschbach Jarrell; C. Hunter Baker

(57) ABSTRACT

Novel compounds that are anti-angiogenic or immunosuppressive are described. Also described are methods for determining if an animal is at risk for a disease involving abnormal angiogenesis or an immune reaction resulting in pathology comprising evaluating an aspect of MetAP2 metabolism or structure; methods for identifying agents that are anti-angiogenic or immunosuppressive comprising evaluating the effect of the agent on an aspect of MetAP2 metabolism; methods for treating a cell having an abnormality in metabolism or structure of MetAP2; and methods for treating abnormal angiogenesis or an immune reaction which results in pathology in an animal. Pharmaceutical compositions are also provided.

4 Claims, 4 Drawing Sheets

OTHER PUBLICATIONS

Marui et al., "Chemical Modification of Fumagillin", I.6-O-Acyl, 6-O-Sulfonyl, 6-O Alkyl, and 6-O-(N-Substituted Carbamoyl) Fumagillos, *Chem. Pharm. Bull.*, 40:96–101, 1992.

Radomski and Jost, "Molecular Cloning of a Murine cDNA Encoding a Novel Protein, 38–2G4, Which Varies with the Cell Cycle", *Exp. Cell Res.*, 220:434–445, 1995.

Ray et al., "The Eukaryotic Initiation Factor 2–Associated 67–kDa Polypeptide ($p^{67}$) Plays a Critical Role in Regulation of Protein Synthesis Initiation in Animal Cells", *Proc. Natl. Acad. Sci. USA*, 89:539–543, 1992.

Shevchenko et al., "Mass Spectrometric Sequencing of Proteins from Silver–Stained Polyacrylamide Gels", *Anal. Chem.*, 68:850–858, 1996.

Shevchenko et al., "Linking Genome and Proteome by Mass Spectrometry–Large–Scale Indentification of Yeast Proteins from Two Dimensional Gels", *Proc. Natl. Acad. Sci., USA*, 93:14440–14445, 1996.

Sin et al., "The Anti–Angiogenic Agent Fumagillin Covalently Binds and Inhibits the Methionine Aminopeptidase, MetAP–2", *Proc. Natl. Acad. Sci. USA*, 94:6099–6103, 1997.

Turk et al., "Binding of Thalidomide to $\alpha_1$ –Acid Glycoprotein May be Involved in its Inhibition of Tumor Necrosis Factor $\alpha$ Production", *Proc. Natl. Acad. Sci. USA.*, 93:7552–7556, 1996.*

Turk et al., "Selective Inhibition of Amino–Terminal Methionine Processing by TNP–470 and Ovalicin in Endothelial Cells", *Chemistry & Biology*, 6:823–833, 1999.*

Vestal et al., Rapid Commun. Mass Spectrom. 9:1044–1050, 1995.*

Wu et al., "Cloning and Characterization of Complementary DNA Encoding the Eukaryotic Initiation Factor 2–Associated 67–kDa Protein ($p^{67}$)", *J. Biol. Chem.* 268: 10796–10801, 1993.*

Zuo et al., "Evidence That Two Zinc Fingers in the Methionine Aminopeptidase from *Saccharomyces Cerevisiae* are Important for Normal Growth", *Mol. Gen. Genetics*, 246: 247–253, 1995.*

* cited by examiner

Fig. 2A

| | | |
|---|---|---|
| SEQ ID NO:1 | Putative Mouse | |
| SEQ ID NO:2 | Rat | |
| SEQ ID NO:3 | Human | |
| SEQ ID NO:4 | S. cerevisiae | |

Putative Mouse  MAGVEQAASF GHLNGDLDPDDREEGTSTAEEAAKKKKKKKGKGAVS    50
Rat             MAGVEEVAASGSHLNGDLDPDDREEGAASTAEEAAKKKKKKKKSKGPSA  50
Human           MAGVEEVAASGSHLNGDLDPDDREEGAASTAEEAAKKKKKKKKSKGPSA  50
S. cerevisiae   MTDAEIENS---------------------------------------  10

Putative Mouse  AMQQELDKESGALVDEVAKQLESQLEEKRDDDEDGDGDADGATGKKK   100
Rat             AGEQEPDKESGASVDEVARQLERSALEDKERDEDEDGDGDGATGKKK   100
Human           AGEQEPDKESGASVDEVARQLERSALEDKERDEDEDGDGDGATGKKK   100
S. cerevisiae   ---------PASDIKELNLNEGVEQQDQAKADESDPVESKKK      43

Putative Mouse  KKKKKRGPKVQTDPPSVPICDLYPNGVFPKGQECEYPPTQDGRTAAW-    149
Rat             KKKKKKRGPKVQTDPPSVPICDLYPNGVFPKGQECEYPPTQDGRTAAW-    149
Human           KKKKKKRGPKVQTDPPSVPICDLYPNGVFPKGQECEYPPTQDGRTAAW-    149
S. cerevisiae   KNKKK---KKKSNVKKIEL---FLDGKYPEI------------LWMD      74

Putative Mouse  ----------RTTSEEKKAL--DQASEEIWNDFREAAAHRQVRKYVMSWIK    188
Rat             ----------RTTSEEKKAL--DQASEEIWNDFREAAEAHRQVRKYVMSWIK   188
Human           ----------RTTSEEKKAL--DQASEEIWNDFREAAEAHRQVRKYVMSWIK   188
S. cerevisiae   YHQDFNLQRTTDEESRYLKRDLERAEHWNDVRKGIEIRRVRRAIKDRV      124

Putative Mouse  PGMTMIEICEKLEDCSRK-------IKENGLNAGLAFPTGCSLNNCAAH    231
Rat             PGMTMIEICEKLEDCSRK-------IKENGLNAGLAFPTGCSLNNCAAH    231
Human           PGMTMIEICEKLEDCSRK-------IKENGLNAGLAFPTGCSLNNCAAH    231
S. cerevisiae   PGMKLMDLADMIENTTRKYTGAENLAMEDPKSQIGEPTGSLNHCAAH      174

Fig. 2B

| | | |
|---|---|---|
| Putative Mouse | YTPNAGDTTVLQYDDICKIDFGTHISGRIIDCAFTVFTFNPKYDLLTAVK | 281 |
| Rat | YTPNAGDTTVLQYDDICKIDFGTHISGRIIDCAFTVFTFNPKYDLLLKAVK | 281 |
| Human | YTPNAGDTTVLQYDDICKIDFGTHISGRIIDCAFTVFTFNPKYDTLLKAVK | 281 |
| S. cerevisiae | FTPNAGDKTVLKYEDMKVDYGVQVNGNIIDSAFTVSFDPQYDNLLAVK | 224 |
| | | |
| Putative Mouse | DATNTGIKCAGIDVRLCDVGEAIQEVMESYEVEIDGKTYQVKPIRNLNGH | 331 |
| Rat | DATNTGIKCAGIDVRLCDVGEAIQEVMESYEVEIDGKTYQVKPIRNLNGH | 331 |
| Human | DATNTGIKCAGIDVRLCDVGEAIQEVMESYEVEIDGKTYQVKPIRNLNGH | 331 |
| S. cerevisiae | DATYTGIKEAGIDVRLTDJGEAIQEVMESYEVEINFETYQVKPCRNLCGH | 274 |
| | | |
| Putative Mouse | SIGPYRIHAGKTVPIVKGGEATRMEEGEVYAIETFGSTGKGVVHDDMECS | 381 |
| Rat | SIGQYRIHAGKTVPIVKGGEATRMEEGEVYAIETFGSTGKGVVHDDMECS | 381 |
| Human | SIGQYRIHAGKTVPIVKGGEATRMEEGEVYAIETFGSTGKGVVHDDMECS | 381 |
| S. cerevisiae | SIAPYRIHGEKSVPIVKNIDTLKMEEGEHFAIETFGSTGRGYMTAGGEVS | 324 |
| | | |
| Putative Mouse | HYMKNFDVGHVPIRLPRTKHLLNVINENFGTLAFCRXWLDRLGESKYLMA | 431 |
| Rat | HYMKNFDVGHVPIRLPRTKHLLNVINENFGTLAFCRRWLDRLGESKYLMA | 431 |
| Human | HYMKNFDVGHVPIRLPRTKHLLNVINENFGTLAFCRRWLDRLGESKYLMA | 431 |
| S. cerevisiae | HYARSAEDHQVMPTLDSAKNLKTIDRNFGTLPFCRRYLDRLGQEKYLFA | 374 |
| | | |
| Putative Mouse | LKNLCDLGIVDPYPPLCDIKGSYTAQFEHTILLRPTCKEVVSRGDDY | 479 |
| Rat | LKNLCDLGIVDPYPPLCDIKGSYTAQFEHTILLRPTCKEVVSRGDDY | 479 |
| Human | LKNLCDLGIVDPYPPLCDIKGSYTAQFEHTILLRPTCKEVVSRGDDY | 479 |
| S. cerevisiae | NNLVRHGLVQDYPPLNDIPGSYTAQFEHTILLAHKKEVVSKGDDY | 422 |

TYPE 2 METHIONINE AMINOPEPTIDASE (METAP2) INHIBITORS AND USES THEREOF

This application is a divisional of application U.S. Ser. No. 09/093,448, filed Jun. 8, 1998, now U.S. Pat. No. 6,207,704 which claims the benefit of U.S. provisional application, U.S. Ser. No. 60/049,159, filed Jun. 9, 1997, each of which is incorporated herein by reference.

The U.S. Government has a paid-up license in this invention and the right in limited circumstances to require the patent owner to license others on reasonable terms as provided for by the terms of Grant No. CA09112 awarded by the National Cancer Institute.

FIELD OF THE INVENTION

This invention relates to agents which inhibit type 2 methionine aminopeptidase (MetAP2), including novel ovalicin and fumagillin derivatives, and to the identification and use of such agents for treating and diagnosing diseases involving abnormal angiogenesis or immune reactions which result in pathology.

BACKGROUND OF THE INVENTION

Angiogenesis is the process of new blood vessel formation. It has been shown to play a pivotal role in certain normal physiological reactions, e.g., wound healing, corpus luteum formation and embryonic development. It has also been reported to play a pivotal role in a variety of pathological conditions, e.g., tumors, diabetic retinopathy, inflammatory diseases and arteriosclerosis. For example, it has been reported that without access to sufficient vasculature, tumor growth is restrained as a result of widespread cell death.

Further, while immune reactions are required to protect animals from deleterious foreign antigens, certain immune reactions can result in pathological conditions, e.g., autoimmune diseases, allergies or tissue graft rejection.

Fumagillin and certain types of fumagillin analogs have been reported to exhibit anti-angiogenic activity, and ovalicin has been reported to exhibit anti-angiogenic and immunosuppressive activity.

There is a need for inhibitors which are more potent, less neurotoxic, more stable, and/or have longer serum half-lives.

SUMMARY OF THE INVENTION

It is an object of the invention to provide compounds which can be used in treating and/or diagnosing diseases involving abnormal angiogenesis or immune reactions resulting in pathology, which are potent, stable, have long serum half-lives, and/or which are polar, thereby being unable to penetrate the blood/brain barrier and thus resulting in low neurotoxicity.

It is yet another object of the invention to provide compounds which inhibit MetAP2 activity.

It is yet another object of the invention to provide compounds which inhibit endothelial cell proliferation.

It is yet another object of the invention to provide a method for identifying agents which are anti-angiogenic or immunosuppressive.

Still another object of the invention is to utilize MetAP2 to aid in identifying agents useful for the treatment and/or diagnosis of diseases involving abnormal angiogenesis or immune reactions which result in pathology.

In one aspect, the invention features a compound of the formula:

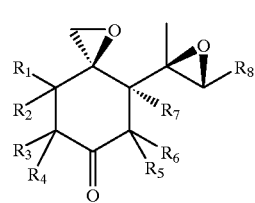

(I)

and pharmaceutically acceptable salts thereof,
wherein
$R_1$, $R_2$, $R_3$, $R_4$, $R_5$ and $R_6$ can be the same or different from each other, and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is hydrogen or an hydroxy group; and $R_8$ is (1) a subtituted alkyl, allyl or alkyne group; or (2) a substituted alkoxyl or thioalkoxyl group, or methylene or ethylene alkoxyl or thioalkoxyl group, wherein the methylene or ethylene can be optionally substituted; or (3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) an alkyl group which can be optionally substituted with $N^+P_1P_2P_3X^-$ or $S^{+P}{}_1P_2X^-$, wherein $P_1$, $P_2$, and $P_3$ can be the same or different and are each an optionally substituted hydrocarbon or heterocyclic group and $X^-$ is a counter anion; or (7) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (8) 2-methyl-1-propenyl or an isobutyl group which can be optionally substituted with $N^+P_1P_2P_3X^-$, $S^+P_1P_2X^-$, wherein $P_1$, $P_2$ and $P_3$ can be the same or different and are each an optionally substituted hydrocarbon or heterocyclic group and $X^-$ is a counter anion; or (9) a benzenesulfonyl, methylsulfonyl or alkyl sufonyl group, with or without a methylene or ethylene substituent, or the corresponding amide or ester, which can be optionally substituted; or

(10) an alkoxycarbonyl or phenoxycarbonyl group with or without a methylene or ethylene substituent, which can be optionally substituted.

A preferred embodiment is a compound having the formula:

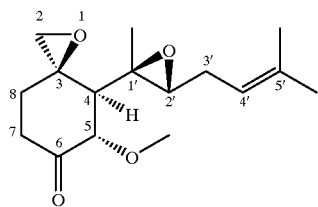

(1)

Another aspect of the invention features a compound of the formula:

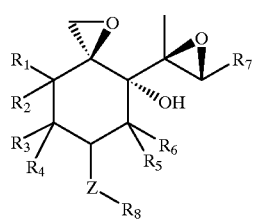

(II)

and pharmaceutically acceptable salts thereof,
wherein

Z is an oxygen and can have R or S configuration;

$R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ and $R_8$ can be the same or different from each other and are:

(1) hydrogen or a substituted alkyl, allyl or alkyne group;

(2) a substituted alkoxyl or thioalkoxyl group, or methylene or ethylene alkoxyl or thioalkoxyl group, wherein the methylene or ethylene can be optionally substituted;

(3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) an alkyl group which can be optionally substituted with $N^+P_1P_2P_3X^-$, $S^+P_1P_2X^-$, wherein $P_1$, $P_2$ and $P_3$ can be the same or different and are each an optionally substituted hydrocarbon or heterocyclic group and $X^-$ is a counter anion; or (7) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether;

(8) 2-methyl-1-propenyl or an isobutyl group which can be optionally substituted with $N^+P_1P_2P_3X^-$, $S^+P_1P_2X^-$, wherein $P_1$, $P_2$ and $P_3$ can be the same or different and are each an optionally substituted hydrocarbon or heterocyclic group and $X^-$ is a counter anion; or (9) a benzenesulfonyl, methylsulfonyl or alkyl sufonyl group, with or without a methylene or ethylene substituent, or the corresponding amide or ester, which can be optionally substituted; or

(10) an alkoxycarbonyl or phenoxycarbonyl group with or without a methylene or ethylene substituent, which can be optionally substituted.

Preferred embodiments are compounds having the formulas:

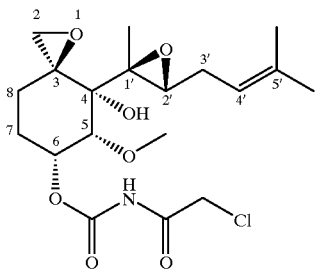

(2)

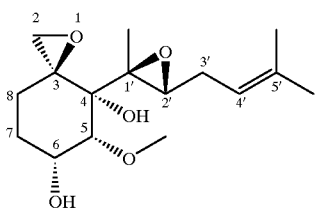

(3)

or

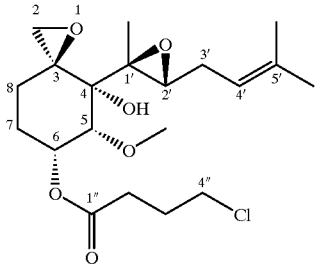

(4)

Another aspect of the invention is a compound of the formula:

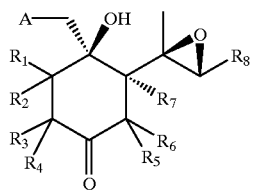

(III)

and pharmaceutically acceptable salts thereof, wherein

A is a halogen, $N^+P_1P_2P_3X^-$ or $S^+P_1P_2X^-$ wherein $P_1$, $P_2$ and $P_3$ can be the same or different and are each an optionally substituted hydrocarbon or heterocyclic group and $X^-$ is a counter anion;

$R_1$, $R_2$, $R_3$, $R_4$, $R_5$ and $R_6$ can be the same or different from each other, and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is hydrogen or an hydroxy group; and $R_8$ is (1) a subtituted alkyl, allyl or alkyne group; or (2) a substituted alkoxyl or thioalkoxyl group, or methylene or ethylene alkoxyl or thioalkoxyl group, wherein the methylene or ethylene can be optionally substituted; or (3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halgen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester or carboxyl salt; or (6) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (7) a benzenesulfonyl, methylsulfonyl or alkyl sufonyl group, with or without a methylene or ethylene substituent, or the corresponding amide or ester, which can be optionally substituted; or (8) an alkoxycarbonyl or phenoxycarbonyl group with or without a methylene or ethylene substituent, which can be optionally substituted.

Another aspect of the invention is a compound of the formula:

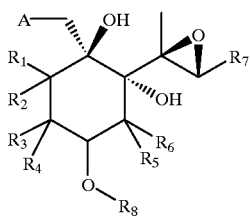

(IV)

and pharmaceutically acceptable salts thereof,
wherein

A is a halogen, $N^+P_1P_2P_3X^-$ or $S^+P_1P_2X^-$ wherein $P_1$, $P_2$ and $P_3$ can be the same or different and are each an optionally substituted hydrocarbon or heterocyclic group and $X^-$ is a counter anion;

$R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is hydrogen or an hydroxy group; and $R_8$ is:

(1) hydrogen or a subtituted alkyl, allyl or alkyne group;

(2) a substituted alkoxyl or thioalkoxyl group, or methylene or ethylene alkoxyl or thioalkoxyl group, wherein the methylene or ethylene can be optionally substituted;

(3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) 2-methyl-1-propenyl or an isobutyl group which can be optionally substituted with hydroxyl, carbamoyl, carbonyldioxyl, thiohydroxyl, amino, alkylamino, dialkylamino, ureido, alkyl, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether;

(7) a benzenesulfonyl, methylsulfonyl or alkyl sufonyl group, with or without a methylene or ethylene substituent, or the corresponding amide or ester, which can be optionally substituted; or (8) an alkoxycarbonyl or phenoxycarbonyl group with or without a methylene or ethylene substituent, which can be optionally substituted.

Preferred embodiments are compounds having the formulas:

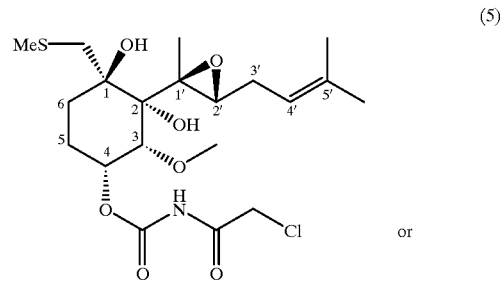

(5)

or

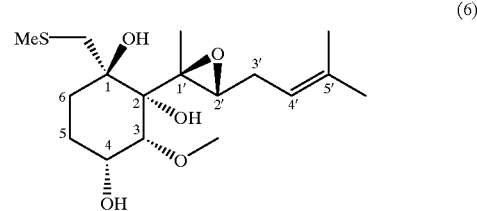

(6)

Another aspect of the invention is a method for determining if an animal is at risk for a disease involving abnormal angiogenesis or an immune reaction resulting in pathology. An animal is provided. An aspect of MetAP2 metabolism or structure is evaluated in the animal. An abnormality in the aspect of MetAP2 metabolism or structure is diagnostic of being at risk for a disease involving abnormal angiogenesis or an immune reaction resulting in pathology.

Another aspect of the invention is a method for identifying an agent that is anti-angiogenic or immunosuppressive. A MetAP2 polypeptide is provided. An agent is provided. The agent is contacted with the MetAP2. The effect of the agent on an aspect of MetAP2 metabolism is evaluated, a change in the aspect of MetAP2 metabolism being indicative of the agent being anti-angiogenic or immunosuppressive.

In certain embodiments, the agent is an ovalicin analog, fumaginone or a fumaginone analog. In certain embodiments, the agent is a MetAP2 polypeptide or a biologically active fragment or analog thereof, a nucleic acid encoding MetAP2 polypeptide or a biologically active fragment or analog thereof, a nucleic acid encoding a MetAP2 regulatory sequence or a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

Another aspect of the invention is a method for evaluating an agent for use in treating a disease involving abnormal angiogenesis or an immune reaction resulting in pathology.

A test cell, cell-free system or animal is provided. An agent is provided. The agent is administered to the test cell, cell-free system or animal in a therapeutically effective amount. The effect of the agent on an aspect of MetAP2 metabolism is evaluated. A change in the aspect of MetAP2 metabolism is indicative of the usefulness of the agent in treating a disease involving abnormal angiogenesis or in inhibiting an immune reaction resulting in pathology.

Another aspect of the invention is a method for evaluating a candidate anti-angiogenic or immunosuppressive agent for the ability to alter the binding of MetAP2 polypeptide to a binding molecule. An agent is provided. A MetAP2 polypeptide is provided. A binding molecule is provided. The agent, MetAP2 polypeptide and binding molecule are combined. The formation of a complex comprising the MetAP2 polypeptide and binding molecule is detected. An alteration in the formation of the complex in the presence of the agent as compared to in the absence of the agent is indicative of the agent altering the binding of the MetAP2 polypeptide to the binding molecule.

Another aspect of the invention is a method for evaluating a candidate anti-angiogenic or immunsuppressive agent for the ability to bind to MetAP2 polypeptide. An agent is provided. A MetAP2 polypeptide is provided. The agent is contacted with the MetAP2 polypeptide. The ability of the agent to bind to the MetAP2 polypeptide is evaluated.

Another aspect of the invention is a method for evaluating a candidate anti-angiogenic or immunosuppressive agent for the ability to bind to a nucleic acid encoding a MetAP2 regulatory sequence. An agent is provided. A nucleic acid encoding a MetAP2 regulatory sequence is provided. The agent is contacted with the nucleic acid. The ability of the agent to bind to the nucleic acid is evaluated.

Another aspect of the invention is a method for treating a cell having an abnormality in metabolism or structure of MetAP2. A cell having an abnormality in structure or metabolism of MetAP2 is provided. An agent, e.g., an ovalicin analog, fumaginone or a fumaginone analog, capable of altering an aspect of MetAP2 metabolism or structure is provided. The agent is administered to the cell in a therapeutically effective amount such that treatment of the cell occurs.

In certain embodiments, the agents are compounds having formulas I, II, III or IV, or pharmaceutically acceptable salts thereof, described herein. In certain preferred embodiments, the agents are compounds having formulas 1, 2, 3, 4, 5 or 6, or pharmaceutically acceptable salts thereof, described herein. In certain embodiments, the agent is a MetAP2 polypeptide or a biologically active fragment or analog thereof, a nucleic acid encoding MetAP2 polypeptide or a biologically active fragment or analog thereof, a nucleic acid encoding a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

Another aspect of the invention is a method for treating abnormal angiogenesis in an animal. An animal in need of treatment for abnormal angiogenesis is provided. An agent, e.g., an ovalicin analog, fumaginone or a fumaginone analog, capable of altering an aspect of MetAP2 metabolism or structure is provided. The agent is administered to the animal in a therapeutically effective amount such that treatment of the abnormal angiogenesis occurs.

Another aspect of the invention is a method for treating an animal at risk for abnormal angiogenesis. An animal at risk for abnormal angiogenesis is provided. An agent, e.g., an ovalicin analog, fumaginone or a fumaginone analog, capable of altering an aspect of MetAP2 metabolism or structure is provided. The agent is administered to the animal in a therapeutically effective amount such that treatment of the animal occurs. Being at risk for abnormal angiogenesis can result from, e.g., a familial history of abnormal angiogenesis, phenotypic symptoms which predispose to abnormal angiogenesis, or a genotype which predisposes to abnormal angiogenesis.

Another aspect of the invention is a method for treating a tumor in an animal. An animal in need of treatment for a tumor is provided. An agent, e.g., an ovalicin analog, fumaginone or a fumaginone analog, capable of altering an aspect of MetAP2 metabolism or structure is provided. The agent is administered to the animal in a therapeutically effective amount such that treatment of the tumor occurs.

Another aspect of the invention is a method for treating an immune reaction which results in pathology in an animal. An animal in need of treatment for an immune reaction which results in pathology is provided. An agent, e.g., an ovalicin analog, fumaginone or a fumaginone analog, capable of altering an aspect of MetAP2 metabolism or structure, is provided. The agent is administered to the animal in a therapeutically effective amount such that treatment of the immune reaction occurs.

Another aspect of the invention is a method for treating an animal at risk for an immune reaction which results in pathology. An animal in need of treatment for an immune reaction which results in pathology is provided. An agent, e.g., an ovalicin analog, fumaginone or a fumaginone analog, capable of altering an aspect of MetAP2 metabolism or structure, is provided. The agent is administered to said animal in a therapeutically effective amount such that treatment of the animal occurs. Being at risk for an immune reaction which results in pathology can result from, e.g., a familial history of such reactions, phenotypic symptoms which predispose to such reactions, or a genotype which predisposes to such reactions.

Another aspect of the invention is a pharmaceutical composition for treating abnormal angiogenesis in an animal comprising a therapeutically effective amount of an agent, e.g., an ovalicin analog, fumaginone or a fumaginone analog, capable of altering an aspect of MetAP2 metabolism or structure in the animal so as to result in treatment of the abnormal angiogenesis, and a pharmaceutically acceptable carrier.

Yet another aspect of the invention is a pharmaceutical composition for treating an immune reaction which results in pathology in an animal comprising a therapeutically effective amount of an agent, e.g., an ovalicin analog, fumaginone or a fumaginone analog, capable of altering an aspect of MetAP2 metabolism or structure in the animal so as to result in treatment of the immune reaction which results in pathology, and a pharmaceutically acceptable carrier.

The above and other features, objects and advantages of the present invention will be better understood by a reading of the following specification in conjunction with the drawings.

BRIEF DESCRIPTION OF THE DRAWINGS

FIG. 2 depicts the putative amino acid sequence of mouse MetAP2 (top sequence)(SEQ ID NO:1) in alignment with the amino acid sequence of rat MetAP2 (second from top sequence)(SEQ ID NO:2), human MetAP2 (third from top sequence)(SEQ ID NO:3) and *Saccharomyces cerevisiae* MetAP2 (bottom sequence)(SEQ ID NO:4).

DETAILED DESCRIPTION

Figure 1:
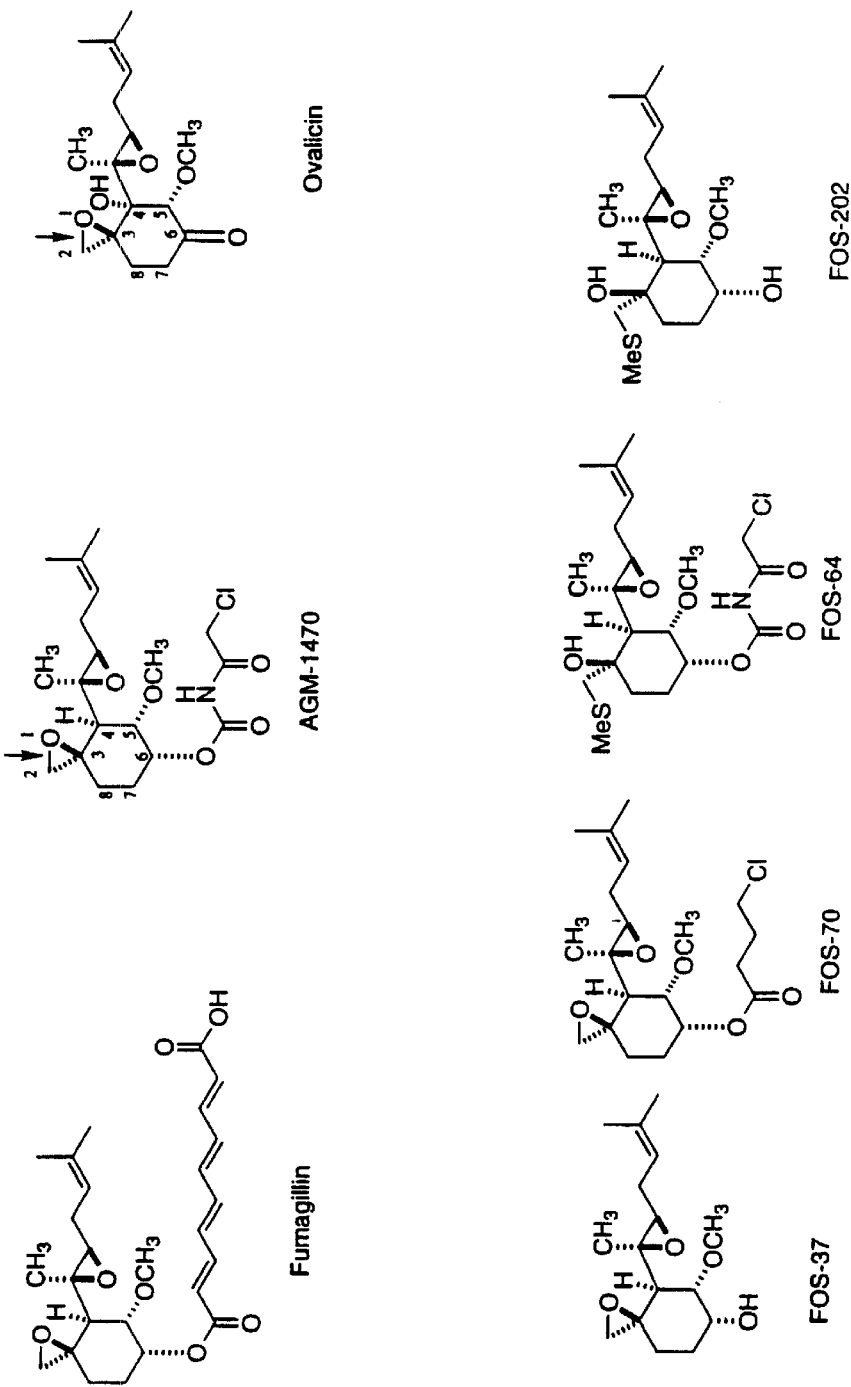
FIG. 1 depicts the formulas of ovalicin, fumagillin, AGM-1470, and various other analogs of fumagillin.

This invention provides a compound of the formula:

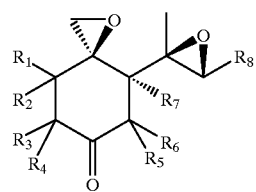

(I)

and pharmaceutically acceptable salts thereof,
wherein $R_1$, $R_2$, $R_3$, $R_4$, $R_5$ and $R_6$ can be the same or different from each other, and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is hydrogen or an hydroxy group; and $R_8$ is (1) a substituted alkyl, allyl or alkyne group; or (2) a substituted alkoxyl or thioalkoxyl group, or methylene or ethylene alkoxyl or thioalkoxyl group, wherein the methylene or ethylene can be optionally substituted; or (3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) an alkyl group which can be optionally substituted with $N^+P_1P_2P_3X^-$ or $S^+P_1P_2X^-$, wherein $P_1$, $P_2$ and $P_3$ can be the same or different and are each an optionally substituted hydrocarbon or heterocyclic group and $X^-$ is a counter anion; or (7) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionalsy substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (8) 2-methyl-1-propenyl or an isobutyl group which can be optionally substituted with $N^+P_1P_2P_3X^-$, $S^+P_1P_2X^-$, wherein $P_1$, $P_2$ and $P_3$ can be the same or different and are each an optionally substituted hydrocarbon or heterocyclic group and $X^-$ is a counter anion; or (9) a benzenesulfonyl, methylsulfonyl or alkyl sufonyl group, with or without a methylene or ethylene substituent, or the corresponding amide or ester, which can be optionally substituted; or

(10) an alkoxycarbonyl or phenoxycarbonyl group with or without a methylene or ethylene substituent, which can be optionally substituted.

A preferred compound of formula I has the formula:

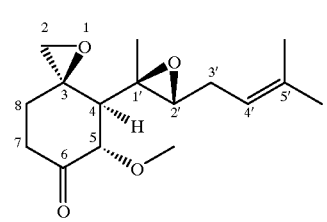

(1)

The invention also provides a compound of the formula:

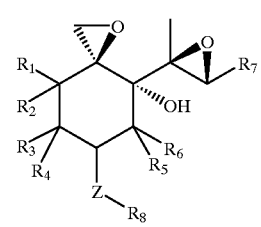

(II)

and pharmaceutically acceptable salts thereof,
wherein

Z is an oxygen and can have R or S configuration;

$R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ and $R_8$ can be the same or different from each other and are:

(1) hydrogen or a subtituted alkyl, allyl or alkyne group;

(2) a substituted alkoxyl or thioalkoxyl group, or methylene or ethylene alkoxyl or thioalkoxyl group, wherein the methylene or ethylene can be optionally substituted;

(3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) an alkyl group which can be optionally substituted with $N^+P_1P_2P_3X^-$, $S^+P_1P_2X^-$, wherein $P_1$, $P_2$ and $P_3$ can be the same or different and are each an optionally substituted hydrocarbon or heterocyclic group and $X^-$ is a counter anion; or (7) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether;

(8) 2-methyl-1-propenyl or an isobutyl group which can be optionally substituted with $N^+P_1P_2P_3X^-$, $S^+P_1P_2X^-$, wherein $P_1$, $P_2$ and $P_3$ can be the same or different and are each an optionally substituted hydrocarbon or heterocyclic group and $X^-$ is a counter anion; or (9) a benzenesulfonyl, methylsulfonyl or alkyl sufonyl group, with or without a methylene or ethylene substituent, or the corresponding amide or ester, which can be optionally substituted; or

(10) an alkoxycarbonyl or phenoxycarbonyl group with or without a methylene or ethylene substituent, which can be optionally substituted.

Preferred compounds of formula II have the formulas:

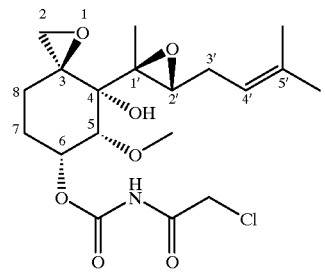

(2)

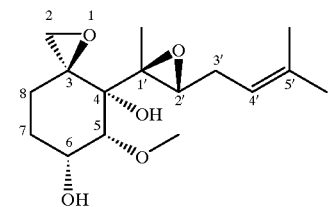

(3)

or

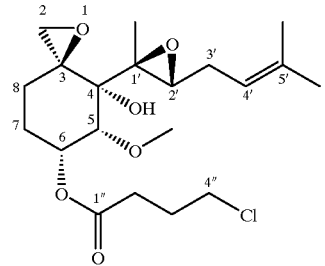

(4)

The invention also provides a compound of the formula:

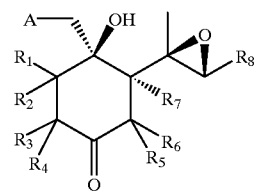

(III)

and pharmaceutically acceptable salts thereof, wherein

A is a halogen, $N^+P_1P_2P_3X^-$ or $S^+P_1P_2X^-$, wherein $P_1$, $P_2$ and $P_3$ can be the same or different and are each an optionally substituted hydrocarbon or heterocyclic group and $X^-$ is a counter anion;

$R_1$, $R_2$, $R_3$, $R_4$, $R_5$ and $R_6$ can be the same or different from each other, and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is hydrogen or an hydroxy group; and $R_8$ is (1) a subtituted alkyl, allyl or alkyne group; or (2) a substituted alkoxyl or thioalkoxyl group, or methylene or ethylene alkoxyl or thioalkoxyl group, wherein the methylene or ethylene can be optionally substituted; or (3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halgen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester or carboxyl salt; or (6) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (7) a benzenesulfonyl, methylsulfonyl or alkyl sufonyl group, with or without a methylene or ethylene substituent, or the corresponding amide or ester, which can be optionally substituted; or (8) an alkoxycarbonyl or phenoxycarbonyl group with or without a methylene or ethylene substituent, which can be optionally substituted.

The invention also provides a compound of the formula:

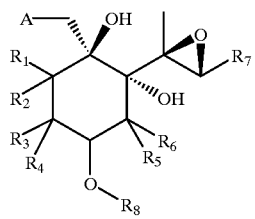

(IV)

and pharmaceutically acceptable salts thereof, wherein

A is a halogen, $N^+P_1P_2P_3X^-$ or $S^+P_1P_2X^-$, wherein $P_1$, $P_2$ and $P_3$ can be the same or different and are each an optionally substituted hydrocarbon or heterocyclic group and $X^-$ is a counter anion;

$R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is hydrogen or an hydroxy group; and $R_8$ is:

(1) hydrogen or a subtituted alkyl, allyl or alkyne group;

(2) a substituted alkoxyl or thioalkoxyl group, or methylene or ethylene alkoxyl or thioalkoxyl group, wherein the methylene or ethylene can be optionally substituted;

(3) an aroyl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether;

(7) a benzenesulfonyl, methylsulfonyl or alkyl sufonyl group, with or without a methylene or ethylene substituent, or the corresponding amide or ester, which can be optionally substituted; or (8) an alkoxycarbonyl or phenoxycarbonyl group with or without a methylene or ethylene substituent, which can be optionally substituted.

Preferred compounds of formula IV have the formulas:

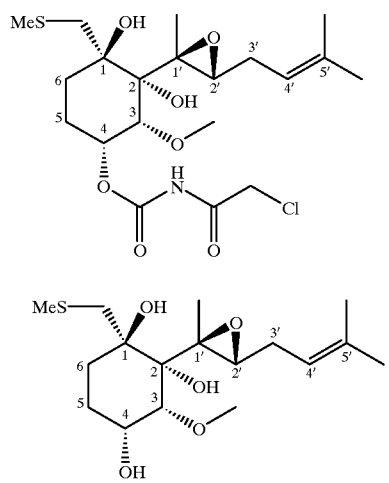

(5)

or (6)

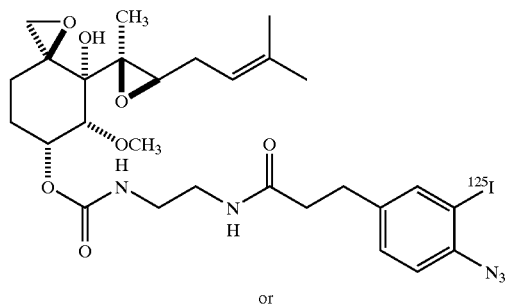

(7)

or

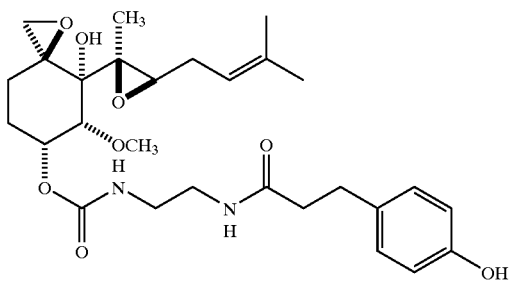

(8)

The compounds of this invention described supra, can be used, e.g., in treating and diagnosing diseases involving abnormal angiogenesis or immune reactions which result in pathology, as described herein. Compounds of formulas 1–6 can be synthesized, e.g., as described in Examples 1–6.

This invention also provides compounds having the formulas:

Compound 7 is an ovalicin photoaffinity label, and compound 8 is an ovalicin photoaffinity label mimic. These compounds can be synthesized, e.g., as described in Example 7. These compounds can be used, e.g., in test assays for measuring the binding compounds to ovalicin, thereby aiding in the identification of target molecules involved in angiogenesis and/or immune reactions, as described in Example 7.

This invention also provides compounds having the formulas:

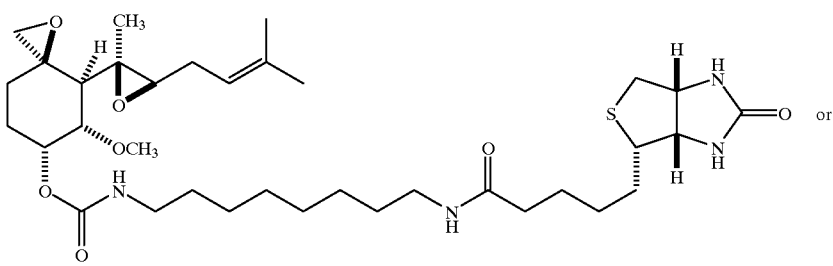

(9)

or

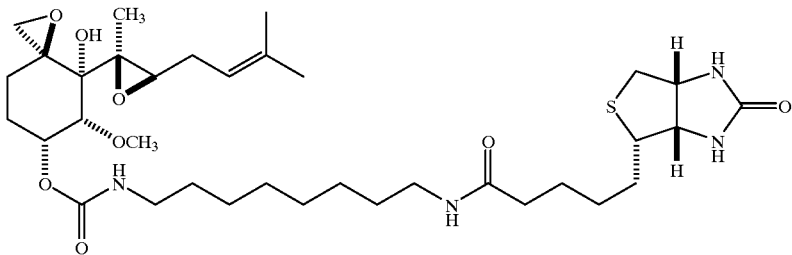

(10)

Compound 9 is a biotin-fumagillin conjugate, and compound 10 is a biotin-ovalicin conjugate. These compounds can be synthesized, e.g., as described in Example 8. These compounds can be used, e.g., to isolate proteins that bind to ovalicin or fumagillin, thereby aiding in identifying target molecules involved in angiogenesis and/or immune reactions, as described in Examples 8 and 9.

This invention also provides a method for determining if an animal is at risk for a disease involving abnormal angiogenesis or an immune reaction resulting in pathology. An animal is provided. An aspect of MetAP2 metabolism or structure is evaluated in the animal. An abnormality in the aspect of MetAP2 metabolism or structure is diagnostic of being at risk for a disease involving abnormal angiogenesis or an immune reaction resulting in pathology.

By angiogenesis is meant formation of new blood vessels. Abnormal angiogenesis can result, e.g., from abnormally accelerated angiogenesis, abnormally stimulated angiogenesis or undesirable angiogenesis. Diseases involving abnormal angiogenesis include, e.g., tumors, diabetic retinopathy, inflammatory diseases and arteriosclerosis.

By immune reaction is meant a response resulting in activation or production of immunocompetent cells, e.g., lymphocytes. Immune reactions which result in pathology can be caused, e.g., by an excess production or recruitment of such immunocompetent cells. Diseases involving such abnormal immune reactions include, e.g., autoimmune diseases, e.g., rheumatoid arthritis, multiple sclerosis and psoriesis; allergies, and tissue graft rejections, e.g., resulting from solid organ or tissue transplantation, or from bone marrow transplantation.

By animal is meant human as well as non-human animals. Non-human animals include, e.g., mammals, birds, reptiles, amphibians and fish. Preferably, the non-human animal is a mammal, e.g., a rodent, e.g., a mouse or rat, a rabbit, a monkey, a dog, a cat or a pig. An animal also includes transgenic non-human animals. The term transgenic animal is meant to include an animal that has gained new genetic material from the introduction of foreign DNA, i.e., partly or entirely heterologous DNA, into the DNA of its cells; or introduction of a lesion, e.g., an in vitro induced mutation, e.g., a deletion or other chromosomal rearrangement into the DNA of its cells; or introduction of homologous DNA into the DNA of its cells in such a way as to alter the genome of the cell into which the DNA is inserted, e.g., it is inserted at a location which differs from that of the natural gene or its insertion results in a knockout. The animal may include a transgene in all of its cells including germ line cells, or in only one or some of its cells. Transgenic animals of the invention can serve as a model for studying the diseases discussed herein. In certain embodiments, the determination for being at risk for the disease discussed herein is done in a prenatal animal.

MetAP2 is the type 2 methionine aminopeptidase/eIF-2α phosphorylation inhibitor. It is a bifunctional protein which has methionine aminopeptidase activity and which inhibits phosphorylation of eIF-2α by HRI. It is shown herein that the methionine aminopeptidase activity of MetAP2 is potently inhibited by an analog of fumagillin, AGM-1470, and ovalicin, which are known inhibitors of angiogenesis due to their inhibition of endothelial cell proliferation. This inhibition is shown herein to be due to covalent binding of AGM-1470 or ovalicin with MetAP2. The novel analogs of this invention also inhibit MetAP2 activity. MetAP2 is also meant to include other members of the MetAP2 family of proteins, e.g., p38-2G4, a proliferation associated protein obtainable from nuclear extracts, having significant homology to the 67 KD MetAP2 protein (Radomski and Jost, Exp. Cell Res. 220:434–445 (1995). Preferably, the type 2 methione aminopeptidase/eIF-2α phosphorylation inhibitor is used in this invention.

By MetAP2 metabolism is meant any aspect of the production, release, expression, function, action, interaction or regulation of MetAP2. These aspects are meant to include, e.g., temporal, site or distribution aspects. The metabolism of MetAP2 includes modifications, e.g., covalent or non-covalent modifications of MetAP2 polypeptide. The terms peptides, proteins and polypeptides are used interchangeably herein. The metabolism of MetAP2 includes modifications, e.g., covalent or non-covalent modifications that MetAP2 induces in other substances. The metabolism of MetAP2 also includes changes in the distribution of MetAP2 polypeptide, and changes MetAP2 induces in the distribution of other substances.

Any aspect of MetAP2 metabolism can be evaluated. The methods used are standard techniques known to those skilled in the art and can be found in standard references, e.g., Ausubel et al., ed., Current Protocols in Mol. Biology, New York: John Wiley & Sons, 1990; Sambrook et al., Mol. Cloning, Cold Spring Harbor Laboratory Press, New York, N.Y. (1989). Examples of MetAP2 metabolism that can be evaluated include the binding activity of MetAP2 polypeptide to a binding molecule; the effect of MetAP2 polypeptide on the posttranslational modification or stability of a target gene; the level of MetAP2 protein; the level of MetAP2 mRNA; or the level of MetAP2 modification, e.g., phosphorylation, acetylation, methylation, carboxylation or glycosylation. By binding molecule is meant any molecule to which MetAP2 can bind, e.g., a nucleic acid, e.g., a DNA regulatory region, a protein, a metabolite, a peptide mimetic, a non-peptide mimetic, an antibody, or any other type of ligand. Binding can be shown, e.g., by electrophoretic mobility shift analysis (EMSA), by the yeast or mammalian two-hybrid or three-hybrid assays, by competition with fumagillin or ovalicin photoaffinity label or biotin-fumagillin or biotin-ovalicin binding. Transactivation of a target gene by MetAP2 can be determined, e.g., in a transient transfection assay in which the promoter of the target gene is linked to a reporter gene, e.g., β-galactosidase or luciferase, and co-transfected with a MetAP2 expression vector. Assays for MetAP2 activity include a methionine amino peptidase assay (Zuo et al., Mol. Gen. Genetics 246:247–253 (1995); a map1 yeast mutant proliferation assay (Li and Chang, Proc. Natl. Acad. Sci. 92:12357–12361 (1995)); endothelial cell proliferation assays (Antoine et al., Cancer Res. 54:2073–2076 (1994); and a mixed lymphocyte reaction assay (coligan et al., (eds.) Current Protocols in Immunulogy, New York: John Wiley & Sons (1991). Levels of MetAP2 protein, mRNA or modification, can, e.g., be measured in a sample, e.g., a tissue sample, e.g., endothelial cells in blood vessels, T and B lymphocytes from blood or lymph organs, heart, muscle or bone joints. In certain embodiments, the evaluations are done in vitro; in other embodiments the evaluations are done in vivo.

In certain embodiments, an aspect of MetAP2 structure is evaluated, e.g., MetAP2 gene structure or MetAP2 protein structure. For example, primary, secondary or tertiary structures can be evaluated. For example, the DNA sequence of the gene is determined and/or the amino acid sequence of the protein is determined. Standard cloning and sequencing methods can be used as are known to those skilled in the art. In certain embodiments, the binding activity of an antisense nucleic acid with the cellular MetAP2 mRNA and/or genomic DNA is determined using standard methods known to those skilled in the art so as to detect the presence or absence of the target mRNA or DNA sequences to which the antisense nucleic acid would normally specifically bind.

The invention also includes a method for identifying an agent that is anti-angiogenic or immunosuppressive. A MetAP2 polypeptide is provided. An agent is provided. The agent is contacted with the MetAP2. The effect of the agent on an aspect of MetAP2 metabolism is evaluated, a change in the aspect of MetAP2 metabolism being indicative of the agent being anti-angiogenic or immunosuppressive.

By anti-angiogenic is meant that angiogenesis is inhibited. By immunosuppressive is meant that an immune reaction is inhibited. Preferably, the MetAP2 polypeptide is substantially pure. By substantially pure is meant that the preparation is at least about 60%, preferably at least about 75%, more preferably at least about 90%, and most preferably at least about 99% by weight MetAP2. The MetAP2 polypeptide can be obtained, e.g., from purification or secretion of naturally occurring MetAP2, from recombinant MetAP2 or from synthesized MetAP2.

Any aspect of MetAP2 metabolism discussed herein can be evaluated. In certain embodiments, the aspect of MetAP2 metabolism that is evaluated is an assay requiring MetAP2, e.g., a methionine aminopeptidase assay. In certain embodiments, the agent is tested for its ability to inhibit cell proliferation, e.g., endothelial cell proliferation, an inhibiting effect being indicative that the agent is anti-angiogenic. In certain embodiments, the agent is tested for its immunosuppressive ability, e.g., in a mixed lymphocyte reaction assay. In certain preferred embodiments, the agent is initially tested for an effect on MetAP2 in general, and then further tested for a specific anti-angiogenic and/or immunosuppressive effect.

In certain embodiments, the agent is an ovalicin analog, fumaginone or a fumaginone analog. By fumaginone is meant the ketone derivative of fumagillin. By fumaginone analog is meant an analog of fumaginone which retains the ketone group. Preferred agents include, e.g., fumaginone and analogs of fumaginone set forth in formulas (I) and (III) and pharmaceutically acceptable salts thereof, and analogs of ovalicin set forth in formulas (II) and (IV) and pharmaceutically acceptable salts thereof, described herein.

In certain embodiments, the agent is a MetAP2 polypeptide or a biologically active fragment or analog thereof, a nucleic acid encoding MetAP2 polypeptide or a biologically active fragment or analog thereof, a nucleic acid encoding a MetAP2 regulatory sequence or a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

The agent can be, e.g., a natural ligand for MetAP2 or an artificial ligand for MetAP2. In certain embodiments, the agent is an antagonist or an agonist.

The invention also includes the agent identified by this method.

The invention also includes a method for evaluating an agent for use in treating a disease involving abnormal angiogenesis or an immune reaction resulting in pathology. A test cell, cell-free system or animal is provided. An agent is provided. The agent is administered to the test cell, cell-free system or animal in a therapeutically effective amount. The effect of the agent on an aspect of MetAP2 metabolism is evaluated. A change in the aspect of MetAP2 metabolism is indicative of the usefulness of the agent in treating a disease involving abnormal angiogenesis or in inhibiting an immune reaction resulting in pathology.

In certain embodiments, the method employs two phases for evaluating an agent for use in treating a disease involving abnormal angiogenesis or for use in inhibiting an immune reaction which results in pathology, an initial in vitro phase and then an in vivo phase. The agent is administered to the test cell or cell-free system in vitro, and if a change in an aspect of MetAP2 metabolism occurs, then the agent is further administered to a test animal in a therapeutically effective amount and evaluated in vivo for an effect of the agent on an aspect of MetAP2 metabolism.

By cell is meant a cell or a group of cells, or a cell that is part of an animal. The cell can be a human or non-human cell. Cell is also meant to include a transgenic cell. The cell can be obtained, e.g., from a culture or from an animal. Animals are meant to include, e.g., natural animals and non-human transgenic animals. In certain embodiments, the transgenic cell or non-human transgenic animal has a MetAP2 transgene, or fragment or analog thereof. In certain embodiments, the transgenic cell or non-human transgenic animal has a knockout for the MetAP2 gene.

The test cell, cell-free system or animal can have a wild type or non-wild type pattern of MetAP2 metabolism.

A non-wild type pattern of MetAP2 metabolism can result, e.g., from under-expression, over-expression, no expression, or a temporal, site or distribution change. Such a non-wild type pattern can result, e.g., from one or more mutations in the MetAP2 gene, in a binding molecule gene, or in any other gene which directly or indirectly affects MetAP2 metabolism. A mutation is meant to include, e.g., an alteration, e.g., in gross or fine structure, in a nucleic acid. Examples include single base pair alterations, e.g., missense or nonsense mutations, frameshifts, deletions, insertions and translocations. Mutations can be dominant or recessive. Mutations can be homozygous or heterozygous.

An agent is meant to include, e.g., any substance, e.g., an anti-angiogenic or anti-immune reaction drug. The agent of this invention preferably can change an aspect of MetAP2 metabolism. Such change can be the result of any of a variety of events, including, e.g., preventing or reducing interaction between MetAP2 and a binding molecule; inactivating MetAP2 and/or the binding molecule, e.g., by cleavage or other modification; altering the affinity of MetAP2 and the binding molecule for each other; diluting out MetAP2 and/or the binding molecule; preventing expression of MetAP2 and/or the binding molecule; reducing synthesis of MetAP2 and/or the binding molecule; synthesizing an abnormal MetAP2 and/or binding molecule; synthesizing an alternatively spliced MetAP2 and/or binding molecule; preventing or reducing proper conformational folding of MetAP2 and/or the binding molecule; modulating the binding properties of MetAP2 and/or the binding molecule; interfering with signals that are required to activate or deactivate MetAP2 and/or the binding molecule; activating or deactivating MetAP2 and/or the binding molecule at the wrong time; or interfering with other receptors, ligands or other molecules which are required for the normal synthesis or functioning of MetAP2 and/or the binding molecule.

Examples of agents include ovalicin analogs, fumaginone and fumaginone analogs. In certain embodiments, the agents are ovalicin analogs which are substituted at the C-6 position or in which the terminal epoxide is opened, or fumaginone analogs in which the terminal epoxide is opened.

In certain embodiments, the agents are compounds having formulas I, II, III or IV, or pharmaceutically acceptable salts thereof, described herein. In certain preferred embodiments, the agents are compounds having formulas 1, 2, 3, 4, 5 or 6, or pharmaceutically acceptable salts thereof, described herein.

In certain embodiments, the agent is a MetAP2 polypeptide or a biologically active fragment or analog thereof, a nucleic acid encoding MetAP2 polypeptide or a biologically active fragment or analog thereof, a nucleic acid encoding a MetAP2 regulatory sequence or a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

The agent can be, e.g., a natural ligand for MetAP2 or an artificial ligand for MetAP2. In certain embodiments, the agent is an antagonist, an agonist or a super agonist.

By a MetAP2 analog is meant a compound that differs from naturally occurring MetAP2 in amino acid sequence or in ways that do not involve sequence, or both. Analogs of the invention generally exhibit at least about 90% homology, preferably at least about 95% homology, and most preferably at least about 99% homology, with a segment of 20 amino acid residues, preferably with more than 40 amino acid residues, or more preferably yet with substantially the entire sequence of a naturally occurring MetAP2 sequence. Non-sequence modifications include, e.g., in vivo or in vitro chemical derivatizations of MetAP2. Non-sequence modifications include, e.g., changes in phosphorylation, acetylation, methylation, carboxylation, or glycosylation. Methods for making such modifications are known to those skilled in the art. For example, phosphorylation can be modified by exposing MetAP2 to phosphorylation-altering enzymes, e.g., kinases or phosphatases.

Preferred analogs include MetAP2 or biologically active fragments thereof, whose sequences differ from the wild-type sequence by one or more conservative amino acid substitutions or by one or more non-conservative amino acid substitutions, deletions, or insertions which do not abolish MetAP2 biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions are shown in Table 1.

TABLE 1

CONSERVATIVE AMINO ACID SUBSTITUTIONS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn, L-NMMA, L-NAME |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Histidine | H | D-His |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |

TABLE 1-continued

CONSERVATIVE AMINO ACID SUBSTITUTIONS

| For Amino Acid | Code | Replace with any of |
|---|---|---|
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tryptophan | W | D-Trp, Phe, D-Phe, Tyr, D-Tyr |
| Tyrosine | Y | D-Tyr, Phe, D-Phe, L-Dopa, His, D-His |
| Valine | V | D-Val, Leu, D-Leu, Ile, D-Ile, Met, D-Met |

Amino acid sequence variants of a protein can be prepared by any of a variety of methods known to those skilled in the art. For example, random mutagenesis of DNA which encodes a protein or a particular domain or region of a protein can be used, e.g., PCR mutagenesis (using, e.g., reduced Taq polymerase fidelity to introduce random mutations into a cloned fragment of DNA; Leung et al., Technique 1:11–15 (1989)), or saturation mutagenesis (by, e.g., chemical treatment or irradiation of single-stranded DNA in vitro, and synthesis of a complementary DNA strand; Mayers et al., Science 229:242 (1985)). Random mutagenesis can also be accomplished by, e.g., degenerate oligonucleotide generation (using, e.g., an automated DNA synthesizer to chemically synthesize degenerate sequences; Narang, Tetrahedron 39:3 (1983); Itakura et al., Recombinant DNA, Proc. 3rd Cleveland Sympos. Macromolecules, ed. A. G. Walton, Amsterdam: Elsevier, pp. 273–289 (1981)). Non-random or directed mutagenesis can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (i) substituting first with conserved amino acids and then with more radical choices depending upon results achieved, (ii) deleting the target residue, (iii) inserting residues of the same or a different class adjacent to the located site, or (iv) combinations of the above.

Methods for identifying desirable mutations include, e.g., alanine scanning mutagenesis (Cunningham and Wells, Science 244:1081–1085 (1989)), oligonucleotide-mediated mutagenesis (Adelman et al., DNA 2:183 (1983)); cassette mutagenesis (Wells et al., Gene 34:315 (1985)), combinatorial mutagenesis, and phage display libraries (Ladner et al., PCT Application No. WO88/06630).

Other analogs within the invention include, e.g., those with modifications which increase peptide stability. Such analogs may contain, e.g., one or more non-peptide bonds (which replace the peptide bonds) in the peptide sequence. Also included are, e.g.: analogs that include residues other than naturally occurring L-amino acids, e.g., D-amino acids or non-naturally occurring or synthetic amino acids, e.g., β or γ amino acids; and cyclic analogs.

Analogs can be made by methods known to those skilled in the art. For example, analogs can be made by in vitro DNA sequence modifications of the MetAP2 gene. For example, in vitro mutagenesis can be used to convert the wild type DNA sequence of MetAP2 into a sequence which encodes an analog in which one or more amino acid residues has undergone a replacement, e.g., a conservative replacement as described in Table 1.

By fragment is meant some portion of the naturally occurring MetAP2 polypeptide. Preferably, the fragment is at least about 60 amino acid residues, more preferably at least about 40 amino acid residues, more preferably yet at least about 20 amino acid residues in length, and most preferably at least about 10 amino acid residues in length. Fragments include, e.g., proteolytic fragments, splicing fragments, other fragments, and chimeric constructs between at least a portion of the relevant gene, e.g., MetAP2, and another molecule. Fragments of MetAP2 can be generated by methods known to those skilled in the art. The ability of a candidate fragment to exhibit a biological activity of MetAP2 can be assessed by methods known to those skilled in the art. Also included are MetAP2 fragments containing residues that are not required for biological activity of the fragment or that result from alternative mRNA splicing or alternative protein processing events.

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNAs which encode an array of fragments. DNAs which encode fragments of a protein can also be generated, e.g., by random shearing, restriction digestion or a combination of the above-discussed methods. For example, fragments of MetAP2 can be made by expressing MetAP2 DNA which has been manipulated in vitro to encode the desired fragment, e.g., by restriction digestion of the DNA sequence of MetAP2.

Fragments can also be chemically synthesized using techniques known in the art, e.g., conventional Merrifield solid phase f-Moc or t-Boc chemistry. For example, peptides of the present invention can be arbitrarily divided into fragments of desired length with no overlap of the fragments, or divided into overlapping fragments of a desired length.

MetAP2 or a biologically active fragment or analog thereof, or a MetAP2 binding molecule or a biologically active fragment or analog thereof, can, e.g., compete with its cognate molecule for the binding site on the complementary molecule, and thereby reduce or eliminate binding between MetAP2 and the cellular binding molecule. MetAP2 and binding molecule can be obtained, e.g., from purification or secretion of naturally occurring MetAP2 or binding molecule, from recombinant MetAP2 or binding molecule, or from synthesized MetAP2 or binding molecule.

An agent can also be a nucleic acid used as an antisense molecule. Antisense therapy is meant to include, e.g., administration or in situ generation of oligonucleotides or their derivatives which specifically hybridize, e.g., bind, under cellular conditions, with the cellular mRNA and/or genomic DNA encoding a MetAP2 polypeptide, or mutant thereof, so as to inhibit expression of the encoded protein, e.g., by inhibiting transcription and/or translation. The binding may be by conventional base pair complementarity, or, for example, in the case of binding to DNA duplexes, through specific interactions in the major groove of the double helix.

In certain embodiments, the antisense construct binds to a naturally-occurring sequence of a MetAP2 gene which, e.g., is involved in expression of the gene. These sequences include, e.g., start codons, stop codons, and RNA primer binding sites.

In other embodiments, the antisense construct binds to a nucleotide sequence which is not present in the wild type gene. For example, the antisense construct can bind to a region of a MetAP2 gene which contains an insertion of an exogenous, non-wild type sequence. Alternatively, the antisense construct can bind to a region of a MetAP2 gene which has undergone a deletion, thereby bringing two regions of the gene together which are not normally positioned together and which, together, create a non-wild type sequence. When administered in vivo to a subject, antisense constructs which bind to non-wild type sequences provide the advantage of inhibiting the expression of a mutant MetAP2 gene, without inhibiting expression of any wild type MetAP2 gene.

An antisense construct of the present invention can be delivered, e.g., as an expression plasmid which, when transcribed in the cell, produces RNA which is complementary to at least a unique portion of the cellular mRNA which encodes a MetAP2 polypeptide. An alternative is that the antisense construct is an oligonucleotide probe which is generated ex vivo and which, when introduced into the cell causes inhibition of expression by hybridizing with the mRNA and/or genomic sequences of a MetAP2 gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA. (See also U.S. Pat. Nos. 5,176,996; 5,264,564; and 5,256,775). Additionally, general approaches to constructing oligomers useful in antisense therapy have been reviewed. (See, e.g., Van der Krol et al., Biotechniques 6:958–976, (1988); Stein et al., Cancer Res. 48:2659–2668 (1988)).

By mimetic is meant a molecule which resembles in shape and/or charge distribution MetAP2 or a binding molecule. The mimetic can be a peptide or a non-peptide. Mimetics can act as therapeutic agents because they can, e.g., competitively inhibit binding of MetAP2 to a binding molecule. By employing, e.g., scanning mutagenesis, e.g., alanine scanning mutagenesis, linker scanning mutagenesis or saturation mutagenesis, to map the amino acid residues of a particular MetAP2 polypeptide involved in binding a binding molecule, peptide mimetics, e.g., diazopine or isoquinoline derivatives, can be generated which mimic those residues in binding to a binding molecule, and which therefore can inhibit binding of the MetAP2 to a binding molecule and thereby interfere with the function of MetAP2. For example, non-hydrolyzable peptide analogs of such residues can be generated using benzodiazepine (see, e.g., Freidinger et al., in Peptides: Chemistry and Biology, G. R. Marshall ed., ESCOM Publisher: Leiden, Netherlands (1988)); azepine (see, e.g., Huffman et al., in Peptides: Chemistry and Biology, G. R. Marshall ed., ESCOM Publisher: Leiden, Netherlands (1988)); substituted gamma lactam rings (see, e.g., Garvey et al., in Peptides: Chemistry and Biology, G. R. Marshall ed., ESCOM Publisher: Leiden, Netherlands (1988)); keto-methylene pseudopeptides (see, e.g., Ewenson et al., J. Med. Chem. 29:295 (1986); Ewenson et al., in Peptides: Structure and Function (Proceedings of the 9th American Peptide Symposium) Pierce Chemical Co. Rockland, Ill. (1985)); β-turn dipeptide cores (see, e.g., Nagai et al., Tetrahedron Lett. 26:647 (1985); Sato et al., J. Chem. Soc. Perkin Trans. 1:1231 (1986)); or β-aminoalcohols (see, e.g., Gordon et al., Biochem. Biophys. Res. Commun. 126:419 (1985); Dann et al., Biochem. Biophys. Res. Commun. 134:71 (1986)).

Antibodies are meant to include antibodies against any moiety that directly or indirectly affects MetAP2 metabolism. The antibodies can be directed against, e.g., MetAP2 or a binding molecule, or a subunit or fragment thereof. For example, antibodies include anti-MetAP2 antibodies and anti-binding molecule antibodies. Antibody fragments are meant to include, e.g., Fab fragments, Fab' fragments, F(ab')$_2$ fragments, F(v) fragments, heavy chain monomers, heavy chain dimers, heavy chain trimers, light chain monomers, light chain dimers, light chain trimers, dimers consisting of one heavy and one light chain, and peptides that mimic the activity of the anti-LBP or anti-binding molecule antibodies. For example, Fab$_2$' fragments of the inhibitory antibody can be generated through, e.g., enzymatic cleavage. Both polyclonal and monoclonal antibodies can be used in this invention. Preferably, monoclonal antibodies are used. Natural antibodies, recombinant antibodies or chimeric-antibodies, e.g., humanized antibodies, are included in this invention. Preferably, humanized antibodies are used when the subject is a human. Most preferably, the antibodies have a constant region derived from a human antibody and a variable region derived from an inhibitory mouse monoclonal antibody. Polyclonal, monoclonal and humanized antibodies are generated by standard methods known to those skilled in the art. Monoclonal antibodies can be produced, e.g., by any technique which provides antibodies produced by continuous cell lines cultures. Examples include the hybridoma technique (Kohler and Milstein, Nature 256:495–497 (1975), the trioma technique, the human B-cell hybridoma technique (Kozbor et al., Immunology Today 4:72 (1983)), and the EBV-hybridoma technique to produce human monoclonal antibodies (Cole et al., in Monoclonal Antibodies and Cancer Therapy, A. R. Liss, Inc., pp. 77–96 (1985)). Preferably, humanized antibodies are raised through conventional production and harvesting techniques (Berkower, I., Curr. Opin. Biotechnol. 7:622–628 (1996); Ramharayan and Skaletsky, Am. Biotechnol. Lab 13:26–28 (1995)). Antibodies to MetAP2 are described in Datta et al., J. Biol. Chem. 264:20620–20624 (1989).

Agents also include inhibitors of a molecule that are required for synthesis, post-translational modification, or functioning of MetAP2 and/or a binding molecule, or activators of a molecule that inhibits the synthesis or functioning of MetAP2 and/or a binding molecule. Agents include, e.g., cytokines, growth factors, hormones, signaling components, kinases, phosphatases, homeobox proteins, transcription factors, translation factors and post-translation factors or enzymes. Agents are also meant to include ionizing radiation, non-ionizing radiation, ultrasound and toxic agents which can, e.g., at least partially inactivate or destroy MetAP2 and/or a binding molecule.

An agent is also meant to include agents which are not entirely MetAP2 specific. For example, an agent may alter other angiogenic or immune related genes or proteins. Such overlapping specificity may provide additional therapeutic advantage. In certain embodiments, the effect is additive. In certain embodiments, it is synergistic.

The invention also includes the agent so identified as being useful in treating a disease involving abnormal angiogenesis or for use in inhibiting an immune reaction which results in pathology.

The invention also includes a method for evaluating a candidate anti-angiogenic or immunosuppressive agent for the ability to alter the binding of MetAP2 polypeptide to a binding molecule. An agent is provided. A MetAP2 polypeptide is provided. A binding molecule is provided. The agent, MetAP2 polypeptide and binding molecule are combined. The formation of a complex comprising the MetAP2 polypeptide and binding molecule is detected. An alteration in the formation of the complex in the presence of the agent as compared to in the absence of the agent is indicative of the agent altering the binding of the MetAP2 polypeptide to the binding molecule.

Altering the binding includes, e.g., inhibiting or promoting the binding. The efficacy of the agent can be assessed, e.g., by generating dose response curves from data obtained using various concentrations of the agent. Methods for determining formation of a complex are standard and are known to those skilled in the art.

The invention also includes the agent so identified as being able to alter the binding of MetAP2 polypeptide to a binding molecule.

The invention also includes a method for evaluating a candidate anti-angiogenic or immunsuppressive agent for the ability to bind to MetAP2 polypeptide. An agent is provided. A MetAP2 polypeptide is provided. The agent is contacted with the MetAP2 polypeptide. The ability of the agent to bind to the MetAP2 polypeptide is evaluated. Binding can be determined, e.g., by measuring formation of a complex by standard methods known to those skilled in the art.

The invention also includes the agent so identified as being able to bind to MetAP2 polypeptide.

The invention also includes a method for evaluating a candidate anti-angiogenic or immunosuppressive agent for the ability to bind to a nucleic acid encoding a MetAP2 regulatory sequence. An agent is provided. A nucleic acid encoding a MetAP2 regulatory sequence is provided. The agent is contacted with the nucleic acid. The ability of the agent to bind to the nucleic acid is evaluated. Binding can be determined, e.g., by measuring formation of a complex by standard methods known to those skilled in the art.

The invention also includes the agent so identified as being able to bind to a nucleic acid encoding a MetAP2 regulatory sequence.

The invention also includes a method for treating a cell having an abnormality in metabolism or structure of MetAP2. A cell having an abnormality in structure or metabolism of MetAP2 is provided. An agent, e.g., an ovalicin analog, fumaginone or a fumaginone analog, capable of altering an aspect of MetAP2 metabolism or structure is provided. The agent is administered to the cell in a therapeutically effective amount such that treatment of the cell occurs.

In certain embodiments, the cell is obtained from a cell culture or tissue culture or an embryo fibroblast. The cell can be, e.g., part of an animal, e.g., a natural animal or a non-human transgenic animal.

In certain embodiments, the agents are compounds having formulas I, II, III or IV, or pharmaceutically acceptable salts thereof, described herein. In certain preferred embodiments, the agents are compounds having formulas 1, 2, 3, 4, 5 or 6, or pharmaceutically acceptable salts thereof, described herein.

In certain embodiments, the agent is a MetAP2 polypeptide or a biologically active fragment or analog thereof, a nucleic acid encoding MetAP2 polypeptide or a biologically active fragment or analog thereof, a nucleic acid encoding a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

The invention also includes a method for treating abnormal angiogenesis in an animal. An animal in need of treatment for abnormal angiogenesis is provided. An agent, e.g., an ovalicin analog, fumaginone or a fumaginone analog, capable of altering an aspect of MetAP2 metabolism or structure is provided. The agent is administered to the animal in a therapeutically effective amount such that treatment of the abnormal angiogenesis occurs.

In certain embodiments, the agents are compounds having formulas I, II, III or IV, or pharmaceutically acceptable salts thereof, described herein. In certain preferred embodiments, the agents are compounds having formulas 1, 2, 3, 4, 5 or 6, or pharmaceutically acceptable salts thereof, described herein.

In certain embodiments, the agent is a MetAP2 polypeptide or a biologically active fragment or analog thereof, a nucleic acid encoding MetAP2 polypeptide or a biologically active fragment or analog thereof, a nucleic acid encoding a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

Treating is meant to include, e.g., preventing, treating, reducing the symptoms of, or curing the abnormal condition. Administration of the agent can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed.

Administration of the agent can be alone or in combination with other therapeutic agents. In certain embodiments, the agent can be combined with a suitable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the animal over a prolonged period without repeated administrations. By a controlled release delivery system is meant that total release of the agent does not occur immediately upon administration, but rather is delayed for some time period. Release can occur in bursts or it can occur gradually and continuously. Administration of such a system can be, e.g., by long acting oral dosage forms, bolus injections, transdermal patches or sub-cutaneous implants.

Examples of systems in which release occurs in bursts include, e.g., systems in which the agent is entrapped in liposomes which are encapsulated in a polymer matrix, the liposomes being sensitive to a specific stimuli, e.g., temperature, pH, light, magnetic field, or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The agent can be suspended in a liquid, e.g., in dissolved form or colloidal form. The liquid can be a solvent, partial solvent or non-solvent. In many cases water or an organic liquid can be used.

The agent can be administered prior to or subsequent to the appearance of abnormal symptoms. In certain embodiments, the agent is administered to patients with familial histories of the abnormal condition, or who have phenotypes that may indicate a predisposition to the abnormal condition, or who have been diagnosed as having a genotype which predisposes the patient to the abnormal condition.

The agent is administered to the animal in a therapeutically effective amount. By therapeutically effective amount is meant that amount which is capable of at least partially preventing or reversing the abnormal condition. A therapeutically effective amount can be determined on an individual basis and will be based, at least in part, on consideration of the species of animal, the animal's size, the animal's age, the agent used, the type of delivery system used, the time of administration relative to the onset of the abnormal symptoms, and whether a single, multiple, or controlled release dose regimen is employed. A therapeutically effective amount can be determined by one of ordinary skill in the art employing such factors and using no more than routine experimentation.

Preferably, the dosage of the agent is about 0.1 to about 1000 mg/kg body weight/day, more preferably is about 0.1 to about 500 mg/kg/day, more preferably yet is about 0.1 to about 100 mg/kg/day, and most preferably is about 0.1 to about 50 mg/kg/day. The specific concentration partially depends upon the particular agent used, as some are more effective than others. The dosage of the agent that is actually administered is dependent at least in part upon the final concentration that is desired at the site of action, the method of administration, the efficacy of the particular agent, the longevity of the particular agent, and the timing of administration relative to the onset of the abnormal symptoms. Preferably, the dosage form is such that it does not substantially deleteriously affect the animal. The dosage can be determined by one of ordinary skill in the art employing such factors and using no more than routine experimentation.

In certain embodiments, various gene constructs can be used as part of a gene therapy protocol to deliver nucleic acids encoding, e.g., either an agonistic or antagonistic form of a MetAP2 polypeptide. Expression vectors can be used for in vivo transfection and expression of a MetAP2 polypeptide in particular cell types so as to reconstitute the function of, or alternatively, abrogate the function of MetAP2 polypeptide in a cell in which non-wild type MetAP2 is expressed. Expression constructs of the MetAP2 polypeptide, and mutants thereof, may be administered in any biologically effective carrier, e.g. any formulation or composition capable of effectively delivering the MetAP2 gene to cells in vivo. Approaches include, e.g., insertion of the subject gene in viral vectors including, e.g., recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or $(Ca)_3(PO_4)_2$ precipitation carried out in vivo. The above-described methods are known to those skilled in the art and can be performed without undue experimentation. Since transduction or transfection of appropriate target cells represents the critical first step in gene therapy, choice of the particular gene delivery system will depend on such factors as the phenotype of the intended target and the route of administration, e.g., locally or systemically. Administration can be directed to one or more cell types, and to one or more cells within a cell type, so as to be therapeutically effective, by methods that are known to those skilled in the art. In a preferred embodiment, the agent is administered to endothelial or immune cells of the animal. For example, a genetically engineered MetAP2 gene is administered to endothelial cells. In certain embodiments, administration is done in a prenatal animal or embryonic cell. It will be recognized that the particular gene constructs provided for in in vivo transduction of MetAP2 expression are also useful for in vitro transduction of cells, such as for use in the diagnostic assays described above.

The invention also includes a method for treating an animal at risk for abnormal angiogenesis. An animal at risk for abnormal angiogenesis is provided. An agent, e.g., an ovalicin analog, fumaginone or a fumaginone analog, capable of altering an aspect of MetAP2 metabolism or structure is provided. The agent is administered to the animal in a therapeutically effective amount such that treatment of the animal occurs. Being at risk for abnormal angiogenesis can result from, e.g., a familial history of abnormal angiogenesis, phenotypic symptoms which predispose to abnormal angiogenesis, or a genotype which predisposes to abnormal angiogenesis.

The invention also includes a method for treating a tumor in an animal. An animal in need of treatment for a tumor is provided. An agent, e.g., an ovalicin analog, fumaginone or a fumaginone analog, capable of altering an aspect of MetAP2 metabolism or structure is provided. The agent is administered to the animal in a therapeutically effective amount such that treatment of the tumor occurs.

The invention also includes a method for treating an immune reaction which results in pathology in an animal. An animal in need of treatment for an immune reaction which results in pathology is provided. An agent, e.g., an ovalicin analog, fumaginone or a fumaginone analog, capable of altering an aspect of MetAP2 metabolism or structure, is provided. The agent is administered to the animal in a therapeutically effective amount such that treatment of the immune reaction occurs.

In certain embodiments, the agents are compounds having formulas I, II, III or IV, or pharmaceutically acceptable salts thereof, described herein. In certain preferred embodiments, the agents are compounds having formulas 1, 2, 3, 4, 5 or 6, or pharmaceutically acceptable salts thereof, described herein.

In certain embodiments, the agent is a MetAP2 polypeptide or a biologically active fragment or analog thereof, a nucleic acid encoding MetAP2 polypeptide or a biologically active fragment or analog thereof, a nucleic acid encoding a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

The invention also includes a method for treating an animal at risk for an immune reaction which results in pathology. An animal in need of treatment for an immune reaction which results in pathology is provided. An agent, e.g., an ovalicin analog, fumaginone or a fumaginone analog, capable of altering an aspect of MetAP2 metabolism or structure, is provided. The agent is administered to the animal in a therapeutically effective amount such that treatment of the animal occurs. Being at risk for an immune reaction which results in pathology can result from, e.g., a familial history of such reactions, phenotypic symptoms which predispose to such reactions, or a genotype which predisposes to such reactions.

The invention also includes a pharmaceutical composition for treating abnormal angiogenesis in an animal comprising a therapeutically effective amount of an agent, e.g., an ovalicin analog, fumaginone or a fumaginone analog, capable of altering an aspect of MetAP2 metabolism or structure in the animal so as to result in treatment of the abnormal angiogenesis, and a pharmaceutically acceptable carrier.

In certain embodiments, the agents are compounds having formulas I, II, III or IV, or pharmaceutically acceptable salts thereof, described herein. In certain preferred embodiments, the agents are compounds having formulas 1, 2, 3, 4, 5 or 6, or pharmaceutically acceptable salts thereof, described herein.

In certain embodiments, the agent is a MetAP2 polypeptide or a biologically active fragment or analog thereof, a nucleic acid encoding MetAP2 polypeptide or a biologically active fragment or analog thereof, a nucleic acid encoding a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

The invention also includes a pharmaceutical composition for treating an immune reaction which results in pathology in an animal comprising a therapeutically effective amount of an agent, e.g., an ovalicin analog, fumaginone or a fumaginone analog, capable of altering an aspect of MetAP2 metabolism or structure in the animal so as to result in treatment of the immune reaction which results in pathology, and a pharmaceutically acceptable carrier.

In certain embodiments, the agents are compounds having formulas I, II, III or IV, or pharmaceutically acceptable salts thereof, described herein. In certain preferred embodiments, the agents are compounds having formulas 1, 2, 3, 4, 5 or 6, or pharmaceutically acceptable salts thereof, described herein.

In certain embodiments, the agent is a MetAP2 polypeptide or a biologically active fragment or analog thereof, a nucleic acid encoding MetAP2 polypeptide or a biologically active fragment or analog thereof, a nucleic acid encoding a biologically active fragment or analog thereof, a binding molecule for MetAP2 polypeptide or MetAP2 nucleic acid, a mimetic of MetAP2 polypeptide or MetAP2 nucleic acid, an antibody for MetAP2 or a binding molecule of MetAP2, or an antisense nucleic acid for MetAP2 or a binding molecule for MetAP2.

The following non-limiting examples further illustrate the present invention.

EXAMPLES

Example 1
Synthesis of (3R,4S,5S)-4-[(1'R,2'S)-1',2'-Epoxy-1',5'-dimethyl-4'-hexenyl]-5-methoxy-1-oxaspiro[2.5]octan-6-one/fumaginone

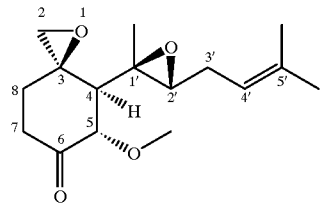

(1)

To a stirred solution of fumagillol (21 mg, 0.074 mmol) and pyridine (0.2 ml) in 4 ml of $CH_2Cl_2$ was added chromium trioxide (50 mg, 0.50 mmol) at 0° C. After stirring for 2 hours in room temperature, the reaction mixture was filtered through a layer of silica gel and was washed three times with additional $CH_2Cl_2$. Removal of solvent by rotovaper in vacuo yielded crude product, which was chromatographed on silica gel (AcOEt/Hexane, 1:3 used as eluent) to give 17 mg (81.5%) product as colorless oil.

$[\alpha]_D$ −65.0 (c=0.1, $CHCl_3$); IR (neat) $cm^{-1}$: 2964, 2925, 1727, 1454, 1381, 1298, 1113, 1035, 986, 874; $^1H$ NMR (500 MHz, $CDCl_3$): 5.19 (1H, t, J=7.3 Hz), 4.08 (1H, d, J=10.3 Hz), 3.51 (3H, s), 3.06 (1H, d, J=4.4 Hz), 2.73 (1H, d, J=4.4 Hz), 2.72–2.64 (1H, m), 2.60 (1H, t, J=6.3 Hz), 2,54–2.48 (1H, m), 2.43–2.35 (1H, m), 2.20–2.02 (2H, 2m), 1.87 (1H, d, J=10.3 Hz), 1.74 (3H, s), 1.75–1.67 (1H, m), 1.65 (3H, s), 1.28 (3H, s); MS(FAB) m/z: 303.3 (M+Na+, 100). The mass is 280.17 and the molecular weight is 280.36.

Example 2
Synthesis of (3S,4R,5R,6R)-4-[(1'S,2'S)-1',2'-Epoxy-1',5'-dimethyl-4'-hexenyl]-5-methoxy-6-O(N-chloro-acetyl)carbamoyl-1-oxaspiror[2.5]octane-4,6-diol

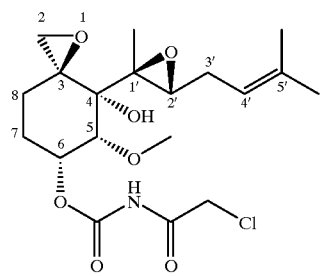

(2)

To a stirred solution of 6-hydroxyovalicin (35 mg, 0.12 mmol) in 3 ml of $CH_2Cl_2$ was added chloroacetyl isocyanate (56 mg, 40 μl, 0.47 mmol) at 0° C. The reaction mixture was stirred for 1.5 hours at room temperature, then diluted with ethyl acetate and washed with saturated aqueous $NaHCO_3$ and brine. The organic phase was dried over anhydrous $MgSO_4$ and concentrated in vacuo. The residue was chromatographed on silica gel (ether/Hexane, 1:2 used as the eluent) to give 39 mg (77.7%) product as colorless oil.

IR (neat) $cm^{-1}$: 3466, 3282, 2964, 2935, 1753, 1719, 1497, 1221, 1197, 1101, 1076; $^1H$ NMR (500 MHz, $CDCl_3$): 8.16 (1H, S), 5.57 (1H, q, J=3.4 Hz), 5.16 (1H, t, J=7.3 Hz), 4.48 (2H, s), 3.65 (1H, d, J=3.9 Hz), 3.48 (3H, s), 3.09 (1H, s), 2.99 (1H, t, J=6.8 Hz), 2.97 (1H, d, J=4.4 Hz), 2.54 (1H, d, J=4.4 Hz), 2.50–2.36 (2H, m), 2.18–2.10 (1H, m), 2.06–1.90 (2H, series of m), 1.73 (3H, s), 1.65 (3H, s), 1.33 (3H, s), 1.08 (1H, m); MS(FAB) m/z: 440.2 (M+Na+, 100). The mass is 417.16 and the molecular weight is 417.89.

Example 3
Synthesis of (3S,4R,5R,6R)-4-[(1'S,2'S)-1',2'-Epoxy-1',5'-dimethyl-4'-hexenyl]-5-methoxy-1-oxaspiror[2.5]octane-4,6-diol

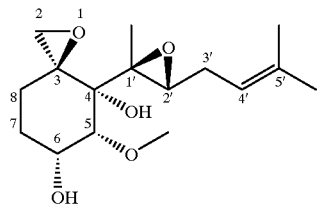

(3)

To a stirred solution of ovalicin (100 mg, 0.34 mmol) in 5 ml of 1,4-dioxane was added sodium borohydride (25.5 mg, 0.67 mmol) at 0° C. The reaction mixture was stirred for 0.5 hours at room temperature. The reaction was then quenched with saturated aqueous $NH_4Cl$ and extracted with $CHCl_3$. The combined organic extracts were dried, filtered, and evaporated to leave a residue which was chromatographed on silica gel (elution with 50% ether in hexane). There was 95 mg (93.7%) of desired product as a colorless oil.

IR (neat) $cm^{-1}$: 3442, 2925, 1439, 1415, 1381, 1201, 1137, 1108, 1030, 981, 923, 801; $^1H$ NMR (500 MHz, $CDCl_3$): 5.16 (1H, t, J=7.5 Hz), 4.45–4.38 (1H, m), 4.02 (1H, d, J=9.3 Hz), 3.57 (1H, s), 3.50 (1H, t, J=3.4 Hz), 3.50 (3H, s), 2.95 (1H, d, J=4.4 Hz), 2.87 (1H, t, J=6.35 Hz), 2.52–2.50 (1H, m), 2.54 (1H, d, J=4.4 Hz), 2.44–2.35 (1H, m), 2.18–2.10 (1H, m), 2.07–2.00 (1H, 2m), 1.84–1.75 (1H, m), 1.73 (3H, s), 1.65 (3H, s), 1.33 (3H, s), 1.01–0.94 (1H, 2m); MS(FAB) m/z: 321.4 (M+Na+, 100). The mass is 298.18 and the molecular weight is 298.38.

Example 4
Synthesis of (3S,4R,5R,6R)-4-[(1'S,2'S)-1',2'-Epoxy-1'5'-dimethyl-4'-hexenyl]-5-methoxy-6-O(4"chlorobutyryl)-1-oxaspiror[2.5]octane-4,6-diol

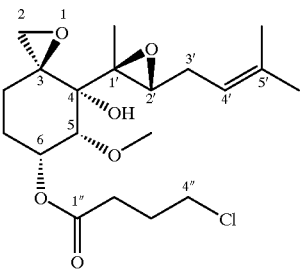

(4)

4-Chlorobutyryl chloride (18 mg, 14 μl, 0.13 mmol) was added to a magnetically stirred solution of 6-hydroxyovalicin (25 mg, 0.084 mmol) and DMAP(15 mg) in $CH_2Cl_2$ (4 ml) at 0° C. After stirring overnight, the reaction was diluted with $CHCl_3$, and was washed with saturated aqueous $NH_4Cl$ solution. The organic phase was dried, filtered, and evaporated. Chromatography of the residue on silica gel (elution with 25% ethyl acetate in hexanes) resulted in 31 mg (91.5%) as a colorless oil.

IR (neat) cm$^{-1}$: 3514, 2935, 1728, 1443, 1376, 1245, 1202, 1173, 1144, 1101, 1004, 956, 927; $^1$H NMR (500 MHz, CDCl$_3$): 5.60 (1H, dd, J=3.4 and 7.8 Hz), 5.18 (1H, t, J=7.5 Hz), 3.63 (1H, d, J=3.9 Hz), 3.61 (2H, t, J=6.5 Hz), 3.46 (3H, s), 3.02 (1H, t, J=6.5 Hz), 2.96 (1H, d, J=4.4 Hz), 2.87 (1H, s), 2.55 (1H, d, J=6.8 Hz), 2.53 (1H, d, J=7.3 Hz), 2.51 (1H, d, J=4.4 Hz), 2.43–2.33 (2H, series of m), 2.18–2.07 (3H, series of m), 1.80–1.84 (2H, series of m), 1.74 (3H, s), 1.65 (3H, s), 1.34 (3H, s), 1.14 (1H, dt, J=4.4, 13.7 Hz); MS(FAB) m/z: 425.1 (M+Na$^+$, 100). The mass is 402.18 and the molecular weight is 402.91.

Example 5

Synthesis of (1R,2S,3R,4R)-1-Methylthiomethylene-2-[(1'S,2'S)-1',2'-epoxy-1',5'-dimethyl-4'-hexenyl]-3-methoxy-4-O-(N-chloroacetyl)carbamoyl-cyclohexane-1,2,4-triol (5)

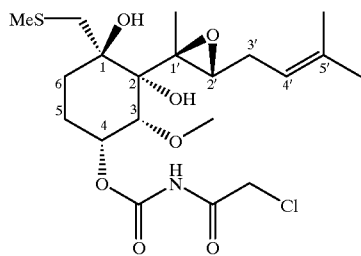

To a stirred solution of methylthiomethylene-trihydroxyovalicin (30 mg, 0.087 mmol) in 2.5 ml of CH$_2$Cl$_2$ was added chloroacetyl isocyanate (11 mg, 8 µl, 0.094 mmol) at 0° C. The reaction mixture was stirred for 1.5 hours at room temperture, then diluted with ethyl acetate and washed with saturated aqueous NaHCO$_3$ and brine. The organic phase was dried over anhydrous MgSO$_4$ and concentrated in vacuo. The residue was chromatographed on silica gel (ether/Hexane, 1:2 used as the eluent) to give 35 mg (86.3%) product as colorless oil.

IR (neat) cm$^{-1}$: 3485, 3263, 2964, 2925, 1753, 1719, 1501, 1376, 1202, 1158, 1105, 1072, 1028; $^1$H NMR (500 MHz, CDCl$_3$): 8.26 (1H, br., s), 5.51 (1H, d, J=2.9 Hz), 5.18 (1H, t, J=7.3 Hz), 4.42 (2H, s), 3.81 (1H, br., s), 3.43 (3H, s), 3.05 (1H, t, J=6.6 Hz), 2.95 (1H, d, J=13.7 Hz), 2.84 (1H, m), 2.48–2.40 (1H, m), 2.23–2.16 (1H, m), 2.14 (3H, s), 2.04–1.97 (1H, dm), 1.95–1.80 (2H, series of m), 1.78–1.50 (3H, series of m), 1.72 (3H, s), 1.66 (3H, s), 1.47 (3H, s); MS(FAB) m/z: 488.1 (M+Na$^+$100). The mass is 465.16 and the molecular weight is 465.99.

Example 6

Synthesis of (1R,2S,3R,4R)-1-Methylthiomethylene-2-[(1'S,2'S)-1',2'-epoxy-1',5'-dimethyl-4'hexenyl]-3-methoxycyclohexane-1,2,4-triol (6)

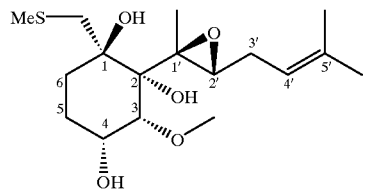

To a stirred solution of 6-hydroxyovalicin (26 mg, 0.087 mmol) in 2 ml of DMF was added thiomethoxide (18 mg, 0.26 mmol) at room temperture. The reaction mixture was stirred for 1.5 hours, then diluted with ethyl acetate and washed with saturated aqueous NaHCO$_3$ and brine. The organic phase was dried over anhydrous MgSO$_4$ and concentrated in vacuo. The residue was chromatographed on silica gel (ethyl acetate/Hexane, 1:2 used as the eluent) to give 21 mg (70.0%) product as colorless oil.

IR (neat) cm$^{-1}$: 3430, 2924, 1441, 1382, 1324, 1154, 1100, 1057, 1037, 833; $^1$H NMR (500 MHz, CDCl$_3$): 5.19 (1H, t, J=7.3 Hz), 4.33–4.29 (1H, m), 3.70 (1H, br., s), 3.49 (3H, s), 2.97 (1H, t, J=6.5 Hz), 2.90 (1H, d, J=13.2 Hz), 2.76 (1H, d, J=13.2 Hz), 2.60–2.40 (2H, m), 2.25–2.17 (1H, m), 2.14 (3H, s), 1.97–1.81 (3H, m), 1.73 (3H, s), 1.66 (3H, s), 1.62–1.54 (1H, m), 1.49 (3H, s); MS(FAB) m/z: 469.5 (M+Na$^+$, 100). The mass is 346.18 and the molecular weight is 346.48.

Example 7

Detection Of a 67-kD Protein That Binds to Both AGM-1470 and Ovalicin by Photoaffinity Labeling of Endothelial Cell Extracts This example illustrates the detection of a 67-kD protein from endothelial cells that binds to both AGM-1470 and ovalicin.

A radioactive photoaffinity label having formula 7 described herein, was attached to ovalicin at the sidechain at the C-6 position. The photoaffinity label of ovalicin was synthesized from its corresponding free amine by analogy as described in Turk et al., Proc. Natl. Acad. Sci. USA 93:7552–7556 (1996). See Example 14. Photoaffinity labeling was performed as follows. To 10 µl cell or tissue extract (10 mg/ml of total protein concentration) was added 5 µl labeling buffer (20 mM Tris-HCl, pH 7.5, 100 mM NaCl), 5 µl 5×cold competitor drug or carrier control (1% EtOH in labeling buffer), and 5 µl ovalicin photolabel (0.2 µCi/µl in 20% MeOH/ddH$_2$O) in the absence of direct light. Reaction mixtures were incubated on ice in the dark for 1 hr and then irradiated at 254 nm (0.2 J/cm$^2$). Reactions were quenched by adding 1.5 µl β-mercaptoethanol followed by 7.5 µl 5×SDS sample buffer and heated in a boiling water bath for 3 min. Samples were analyzed by 10% SDS/PAGE, followed by autoradiography.

To ensure that addition of the photoaffinity label did not significantly abrogate the activity of ovalicin, a mimic of the photoaffinity label having formula 8 described herein, was tested in a bovine aortic endothelial cell (BAEC) proliferation assay (Antoine et al., Cancer Res. 54:2073–2076 (1994)), as follows. BAEC were trypsinized and plated into 96-well plates at a density of 2000 cells per well. After the cells adhered to the plate, compounds dissolved in ethanol (final concentration of 0.5%) were added to the cultures. Three days later, 25 µl of 2.5 mg/ml (3-[4,5-Dimethylthiazol-2-yl]-2,5-diphehyl tetrazolium bromide (MTT) solution was added to the cultures. After an additional 4 hr incubation, 100 μl of 10% SDS/0.01 N HCl solution was added to the culture. The absorbance at 600 nm was determined 12 hr later using a Titertek Multiscan Plus plate reader. The photoaffinity label mimic retained significant, albeit decreased, activity in comparison with ovalicin.

From extracts prepared from BAEC, a number of proteins were labeled by the ovalicin photoaffinity probe. Preincubation of cell extract with excess ovalicin led to the disappearance of a single labeled band of approximately 67 kD (p67), indicating that the labeling of p67 was mediated by the specific binding of ovalicin to the protein. Significantly, treatment of cell extract with AGM-1470 also abrogated p67 labeling, indicating that both AGM-1470 and ovalicin bind competitively to the same target protein.

Example 8
Isolation of p67 from Mouse Embryo Extract and Its Identification as MetAP2/Inhibitor of eIF-2α Phosphorylation This example illustrates that the 67-kD protein that binds to both AGM-1470 and ovalicin is MetAP2.

Extracts were prepared from mouse embryos (14.5 d.p.c.) so as to obtain large amounts of protein for isolation of p67. It was reasoned that the target of AGM-1470 and ovalicin should be abundant during a period of embryogenesis known to involve extensive angiogenesis (Breier et al., Development 114:521–532 (1992)). Using the ovalicin photoaffinity probe described in Example 7, an increased amount of p67 was indeed detected in mouse embryo extracts compared to BAEC extracts. To facilitate the isolation of p67, a biotin conjugate of ovalicin, having formula 9 described herein, and a biotin conjugate of fumagillin, having formula 10 described herein, as affinity reagents were synthesized as described in Example 15. When tested in the BAEC proliferation assay, both the biotin-fumagillin and biotin-ovalicin conjugates were found to retain significant activity. The biotin conjugates were incubated with mouse embryonic extract and bound proteins were isolated by the addition of immobilized streptavidin as follows. Mouse embryo extracts were prepared from 14.5 d.p.c. mouse embryos. Embryos were dissected and dounce homogenized (30 strokes) in 4 ml/g lysis buffer (20 MM Tris·HCl, pH 7.1, 100 mM KCl, 0.2% Triton X-100, 2 μg/ml leupeptin, 2 μg/ml aprotinin, 2 μg/ml soybean trypsin inhibitor). Lysates were centrifuged at 10,000×g for 20 min. The resulting supernatant was centrifuged at 50,000×g for 30 min. The supernatant was either used immediately or frozen at –80° C. for storage. 200 μl of extract was incubated for 30 min with 50 μM competitor or ethanol control at 4° C. Following competition, the extract was incubated with the conjugate ligands (1 μM) for 1 hr at 4° C. 40 μl of immobilized streptavidin (1:1 in lysis buffer) was added and the mixture was incubated at 4° C. for 1 hr. The beads were pelleted at 10,000 rpm in a microcentrifuge for 5 min and washed twice with 600 μl lysis buffer for 5 min. 40 μl of 1×SDS sample buffer was added and the samples were boiled for 10 min. 25 μl of the mixture was loaded on a 12% SDS-PAGE gel and silver stained. A 67-kD protein bound by biotin-fumagillin was visible upon silver staining of the SDS-polyacrylamide gel, and its binding was competed by both AGM-1470 and ovalicin. Similarly, p67 was retained by the biotin-ovalicin conjugate bound to immobilized streptavidin in an AGM-1470 and ovalicin-sensitive manner. Thus, the results obtained with the biotin conjugates were consistent with the observations made with ovalicin photoaffinity labeling, namely that p67 binds to both AGM-1470 and ovalicin.

To obtain a sufficient amount of p67 for identification, the biotin-fumagillin binding experiment was scaled up and ca. 600 ng of p67 was purified from mouse embryo extract. The partially purified p67 was subjected to SDS-PAGE and the 67-kD band was excised after silver staining. This sample was subjected to in-gel digestion with trypsin, and the resulting tryptic fragments were extracted from the gel (Shevchenko et al., Proc. Natl. Acad. Sci. USA 93:14440–14445 (1996)). The peptide mixture thus obtained was analyzed by matrix-assisted laser desorption/ionization-time of flight (MALDI-TOF) mass spectrometry as follows.

The affinity binding experiment was scaled up by using 3 mL of mouse embryo extract (16 mg/mL) and increasing the amount of biotin-fumagillin, immobilized streptavidin and other reagents and solutions proportionally. The partially purified p67 was released from immobilized streptavidin by boiling in sample buffer for 10 min before loading onto a 10% SDS-polyacrylamide gel. After electrophoresis, the gel was silver stained to visualize p67. The 67-kD band was excised, reduced and alkylated with iodoacetamide, followed by digestion with trypsin and extraction as previously described (Shevchenko et al., Anal. Chem. 68:850–858 (1996)). The extract of the tryptic peptide mixture was dried in a Speedvac and the residue was dissolved in 3.5 μl of 7% aqueous formic acid. About 0.5 μl of this solution and 0.5 μl of the standard (ACTH 4–10 and 18–39, 50–100 fmol each) were placed onto a thin film of a-cyano-4-hydroxycinnamic acid deposited on the sample plate of a PerSeptive Biosystems Voyager-Elite MALDI-TOF mass spectrometer and evaporated to dryness. The instrument was operated in the reflectron mode with delayed extraction (Vestal et al., Rapid Commun. Mass Spectrom. 9:1044–1050 (1995)). Under these conditions, the resolution was at least >4000, sufficient to resolve the isotopic multiplets with the mass accuracy being over 50 ppm.

The resulting spectrum exhibited 22 distinct peaks corresponding to [M+H]$^+$ ions of peptides. Those at m/z 842.52, 882.59 and 1010.37 were common background peaks, and m/z 962.43 and 2465.2 represent the internal standards (ACTH 4–10 and 18–39). The remaining 17 m/z values were used to search the EMBL protein database, which revealed that 16 of these values fit those predicted for both the rat and human MetAP2 (Swiss-prot accession No. P38062 and P50579, respectively), which has also been shown to inhibit the phosphorylation of eIF-2α, thus positively regulating protein synthesis (Wu et al., J. Biol. Chem. 268:10796–10801 (1993); Li and Chang, Biochim. Biophys. Acta. 1260:333–336 (1995); Arfin et al., Proc. Natl. Acad. Sci. USA 92:7714–7718 (1995)). These [M+H]$^+$ ions corresponded to 15 different tryptic peptides derived from either human or rat MetAP2. The peaks at m/z 2136.15 and 2122.11 represent the same peptide (452–469) in which the C-terminal Cys468 has reacted partly with monomeric acrylamide. The only peak unaccounted for, m/z 1228.68, may be a contaminant or a peptide from a region that bears a posttranslational modification.

The rat MetAP2, a 478-amino acid glycoprotein with a calculated molecular mass of 53 kD, has been shown to migrate at 67 kD by SDS-PAGE (Wu et al., J. Biol. Chem. 268:10796–10801 (1993)). No mouse homolog of MetAP2 has yet been cloned, but by searching the expressed sequence tagged (EST) database, a putative open reading frame (ORF) was generated by aligning overlapping sequences. The human MetAP2 sequence (Swiss-prot Accession No. P50579) was used to search the EST database. A total of 13 overlapping mouse clones were found (Accession numbers: AA175951, AA172540, AA023796, AA185067, AA175099, AA138570, L26708, AA204267, AA175131, AA212018, AA242695, AA408613 and D21545). They were assembled into a single cDNA encoding the full length MetAP2. Comparison of this putative mouse ORF with the known sequences of human, rat, and yeast MetAP2 indicated that this protein is highly conserved among eukaryotes. See FIG. 2. The three mammalian proteins showed greater than 93% sequence identity, and the yeast MetAP2 sequence possessed greater than 55% identity with the human sequence. All fourteen tryptic peptides identified by mass spectrometry matched the putative mouse ORF exactly. Therefore, a mouse homolog of MetAP2 had been identified.

To confirm the identity of the common binding protein for both AGM-1470 and ovalicin as MetAP2, the binding assay with both biotin-fumagillin and biotin-ovalicin conjugates were repeated and the protein retained on streptavidin beads was analyzed by Western blot with anti-human MetAP2 polyclonal antibodies as follows. Recombinant human MetAP2 was expressed and purified as described in (Li and Chang, Biochem. Biophys. Res. Commun. 227:152–159 (1996)). Samples were transferred to nitrocellulose at 50V for 1 hr at 4° C. The nitrocellulose was treated overnight with blocking solution (5% BSA, 2% Nonfat milk, 0.02% $NaN_3$ in PBS). The membrane was incubated with rabbit anti-human MetAP2 polyclonal antibodies (1:500) for 1 hr at room temperature, followed by incubation with sheep anti-rabbit IgG-HRP. MetAP2 was visualized with the chemilluminescent ECL kit (Amersham, Arlington Heights, Ill.) as per manufacturer's instructions. The mouse p67 which was bound by both biotin-fumagillin and biotin-ovalicin conjugates reacted with the anti-human MetAP2 antibodies. Competition with AGM-1470 and ovalicin led to the elimination of the cross-reacting band. The mouse p67 was also shown to migrate on SDS-PAGE at the same position as authentic human recombinant MetAP2. These experiments established that the common 67-kD binding protein of both fumagillin and ovalicin is identical to MetAP2/inhibitor of eIF-2α phosphorylation.

Example 9
AGM-1470 and Ovalicin Bind Covalently To MetAP2

This example illustrates that AGM-1470 and ovalicin bind covalently to MetAP2.

Since both AGM-1470 and ovalicin possess potentially reactive epoxide groups (see FIG. 1, arrows) that are capable of covalently modifying amino acid sidechains, these drugs were tested to determine if they bind to MetAP2 covalently. The biotin conjugates as described in Example 8 were incubated with recombinant human MetAP2 alone, or in the presence of either AGM-1470 or ovalicin. The protein samples were boiled in a sample buffer containing SDS and β-mercaptoethanol, subjected to SDS-PAGE, and transferred to nitrocellulose. Probing directly with streptavidin-horseradish peroxidase allowed for the visualization of the protein samples that had been incubated with the biotin-fumagillin or biotin-ovalicin conjugates, but not those that had been incubated with free biotin or in the presence of competitors. As a control, the presence of MetAP2 in each sample was confirmed using anti-MetAP2 antibodies. Since the drug-protein complex was maintained under denaturing conditions, it was concluded that AGM-1470 and ovalicin bound to MetAP2 covalently. Experimental details are described as follows.

100 ng of recombinant human MetAP2 was incubated in 40 μl binding buffer (20 mM Tris·HCl, pH 7.1, 100 mM KCl, 0.2% Triton X-100) in the presence or absence of competitors for 1 hr followed by incubation with the biotin conjugates (1 μM) at 4° C. for 2 hr. 40 μl of 2×SDS sample buffer containing β-mercaptoethanol was added and the samples were boiled for 10 min. Following SDS-PAGE, the samples were transferred to nitrocellulose at 50V for 1 hr at 4° C. and blocked overnight in blocking solution (5% BSA, 2% Nonfat milk, 0.02% $NaN_3$ in PBS). The membrane was incubated with rabbit anti-human MetAP2 antibodies (1:500) for 1 hr at room temperature, followed by incubation with sheep anti-rabbit IgG-HRP or incubated with streptavidin-HRP (1:1000) for 1 hr and visualized with the chemilluminescent ECL kit (Amersham, Arlington Heights, Ill.), as per manufacturer's instructions.

Example 10
Assessment of the Effect of AGM-1470 and Ovalicin on the Two Activities of MetAP2

This example illustrates that AGM-1470 and ovalicin inhibit the methionine aminopeptidase activity of MetAP2, but that they do not affect the ability of MetAP2 to inhibit the phosphorylation of eIF-2α by heme-regulated inhibitor kinase.

Since MetAP2 is a bifunctional protein, the effect of AGM-1470 and ovalicin on its two activities was assessed. First, the effect of AGM-1470 and ovalicin on the methionine aminopeptidase activity of recombinant human MetAP2 was tested. Recombinant human MetAP2 was expressed and purified from insect cells as described in Li and Chang, Biochem. Biophys. Res. Commun. 227:152–159 (1996). Various amounts of ovalicin and AGM-1470 were added to buffer H (10 mM Hepes, pH 7.35, 100 mM KCl, 10% glycerol, and 0.1 M $Co^{2+}$) containing 1 nM of purified recombinant human MetAP2 and incubated at 37° C. for 30 min. To start the enzymatic reaction, Met-Gly-Met-Met was added to a concentration of 1 mM to the reaction mixture. Released methionine was quantified at different time points (0, 2, 3 and 5 min) using the method of Zuo et al., Mol. Gen. Genetics 246:247–253 (1995)). Using the tetrapeptide substrate (Li and Chang, Biochim. Biophys. Res. Commun. 227:152–159 (1996)), it was found that both drugs potently inhibit the methionine aminopeptidase activity of MetAP2. The $IC_{50}$ values were estimated at 1 nM for AGM-1470 and 0.4 nM for ovalicin when 1 nM of recombinant human MetAP2 was used in the assay.

In addition to its methionine aminopeptidase activity, MetAP2 has been shown to inhibit the phosphorylation of eIF-2α by heme-regulated inhibitor kinase (HRI) in vitro (Datta et al., Proc. Natl. Acad. Sci. USA 85:3324–3328 (1988); Ray et al., Proc. Natl. Acad. Sci. USA 89:539–543 (1992)). Recombinant human MetAP2 was incubated with AGM-1470 or ethanol carrier alone and dialyzed into 20 mM Tris·HCl, pH 7.8, 100 mM KCl. Modified or control MetAP2 (0.6 μg) was incubated with purified eIF-2 (0.3 μg) in 20 mM Tris·HCl, pH 7.8, 40 mM KCl, and 2 mM $MgAC_2$ on ice for 1 hr. Recombinant HRI (0.25 ng) and [γ-$^{32}$P]ATP were then added to a final total volume of 20 μl and the reaction mixture was further incubated at 37° C. for 10 min. The labeled eIF-2α was analyzed by 10% SDS-PAGE followed by autoradiography. The phosphorylated bands were quantified by NIH Image 1.60 software. MetAP2 bound by AGM-1470 was as effective as unbound MetAP2 in inhibiting phosphorylation of eIF-2α by HRI, without affecting HRI autophosphorylation. These results ruled out the possibility that modulation of eIF-2α phosphorylation by MetAP2 was directly responsible for the inhibition of endothelial cell proliferation by AGM-1470.

Example 11
Determination of the Specificity of AGM-1470 and Ovalicin For the Type 2 MetAP This example illustrates that AGM-1470 and ovalicin specifically inhibit the enzymatic activity of MetAP2 but do not affect MetAP1 in vitro and in vivo in yeast.

Two types of MetAPs have been found in eukaryotes, including the yeast *Saccharomyces cerevisiae* (Chang et al., J. Biol. Chem. 265:19892–19897 (1990); Chang et al., J. Biol. Chem. 267:8007–8011 (1992); Li and Chang, Biochim. Biophys. Acta. 1260:333–336 (1995); Li and Chang, Proc. Natl. Acad. Sci. USA 92:12357–12361 (1995); Arfin et al., Proc. Natl. Acad. Sci. USA 92:7714–7718 (1995)).

Binding of MetAP2, but not MetAP1, to AGM-1470 and ovalicin was detected using photoaffinity labeling and affinity purification, indicating that these drugs were specific for MetAP2. To further test the specificity of these drugs, both wild type and mutant yeast strains lacking either MetAP1 (map1) or MetAP2 (map2) were plated onto media containing the two drugs. Wild-type [YPH500 (MATα ura3-52 lys2-801 ade2-101 trpl-Δ63 his3-Δ200 leu2-Δ1), map1 null [XLP101 (map1::HIS3)], and map2 null [XLP201 (map2::URA3)] yeast cells were grown in YEPD at 30° C. to $A_{600}$ of 1, and plated onto a YEPD plate, and YEPD plates containing 50 nM of ovalicin or AGM 1470. The plates were incubated at 30° C. for four days. While wild type and map2 mutant yeast were resistant to 50 nM of either AGM-1470 or ovalicin, the growth of the map1 mutant was completely inhibited by these drugs. These results indicated that yeast MetAP2, but not MetAP1, was a target for both AGM-1470 and ovalicin in vivo.

AGM-1470 and ovalicin were also tested with recombinant yeast MetAP1 and MetAP2 in vitro. No inhibition of MetAP activity of the type 1 enzyme using concentrations of AGM-1470 and ovalicin up to 10 $\mu$M was observed. In comparison, the yeast MetAP2 enzyme was completely inhibited at concentrations as low as 5 nM, consistent with the in vivo results indicating that the drugs were specific for MetAP2.

Example 12
Pharmacological Correlation Between Inhibition of MetAP2 Enzymatic Activity and Inhibition of Endothelial Cell Proliferation Using Fumagillin and Ovalicin Analogs This example illustrates that synthetic analogs of fumagillin and ovalicin displayed a significant correlation between the potency for inhibition of endothelial cell proliferation and the potency for the inhibition of MetAP2 methionine aminopeptidase activity, supporting the conclusion that inhibition of this enzymatic activity mediates the anti-angiogenic activity of AGM-1470 and ovalicin.

As shown above, the fact that both AGM-1470 and ovalicin specifically inhibited the enzymatic activity of MetAP2 without affecting its protective effect on eIF-2α phosphorylation, indicated that this effect mediated the anti-angiogenic activities of these drugs. To further test this conclusion, a series of synthetic analogs of both fumagillin and ovalicin, having formulas 1, 2, 3, 4, 5 and 6, described herein, were synthesized as described in Examples 1–6. Additional fumagillin analogs, FOS-37, FOS-70, FOS-64 and FOS-202, were also synthesized. (See FIG. 1). Synthesis was according to the procedures as described in Mauri et al., Chem. Pharm. Bull. 40:96–101 (1992); Mauri et al., Chem. Pharm. Bull. 43:588–593 (1995). All the analogs were tested for the inhibition of MetAP2 activity in vitro and inhibition of BAEC proliferation in cell culture as described above.

The results are shown in Table 2.

TABLE 2

Potency of Fumagillin and Ovalicin Analogs for Inhibition of BAEC Proliferation and MetAP2 Enzymatic Activity

| Compound | Proliferation IC$_{50}$ (nM) | MetAP2 IC$_{50}$ (nM) |
|---|---|---|
| AGM-1470 | 0.037 ± 0.0024 | 1.0 ± 0.3 |
| Ovalicin | 0.018 ± 0.0059 | 0.4 ± 0.2 |
| FOS-72 (formula 1) | 0.013 ± 0.0015 | 6 ± 2 |
| FOS-68 (formula 2) | 0.46 ± 0.26 | 2.0 ± 0.8 |
| FOS-69 (formula 4) | 0.31 ± 0.066 | 0.10 ± 0.03 |
| FOS-70 | 0.12 ± 0.01 | 3.5 ± 1.8 |
| FOS-37 | 9.5 ± 4.6 | 8 ± 2 |
| FOS-34 (formula 3) | 2.2 ± 1.4 | 4 ± 1 |
| FOS-64 | 110 ± 18 | 3,000 ± 1,000 |
| FOS-67 (formula 5) | 40 ± 4 | 400 ± 200 |
| FOS-201 (formula 6) | 56 ± 34 | 45 ± 12 |
| FOS-202 | 2,800 ± 2,300 | 5,000 ± 2,000 |

IC$_{50}$s were calculated as the average of at least three experiments fit using Deltagraph Pro 3.5 software.

Figure 3:
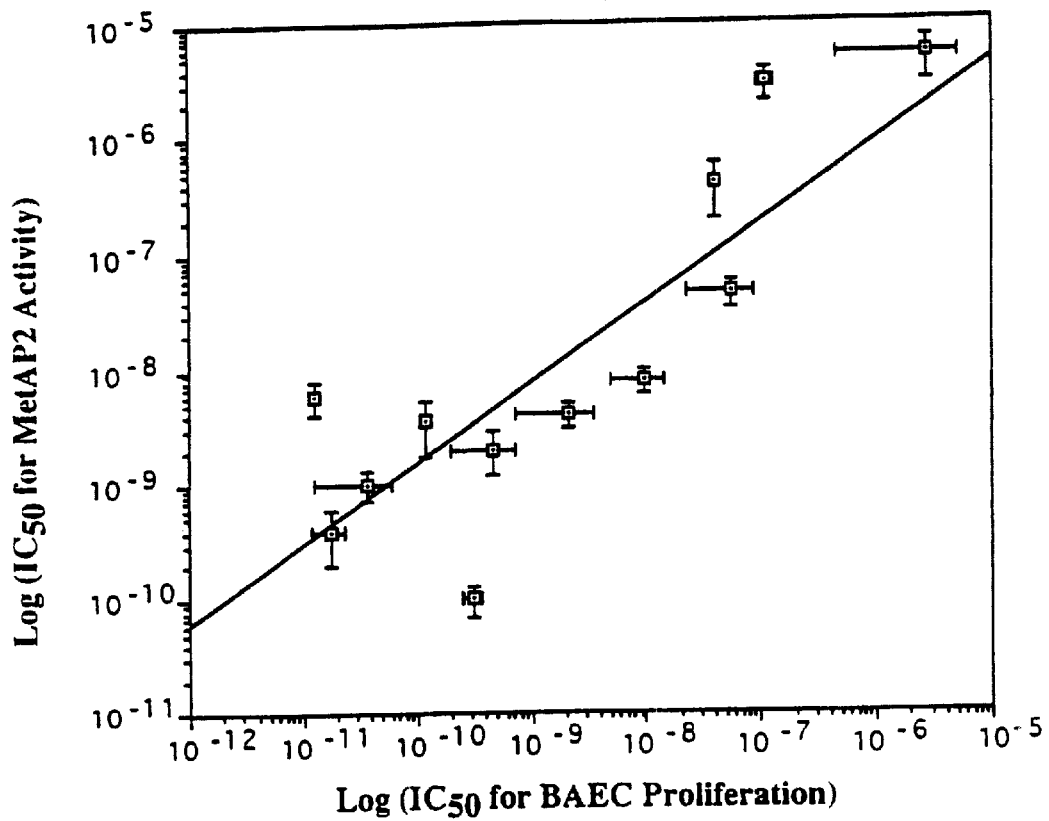
FIG. 3 is a graph depicting the correlation between the potency for inhibition of endothelial cell proliferation and the potency for the inhibition of methionine aminopeptidase activity by a series of synthetic fumagillin and ovalicin analogs.

A significant correlation (Students t test P<0.001) was found between the potency for the inhibition of BAEC proliferation and the potency for the inhibition of methionine aminopeptidase activity (see FIG. 3). Importantly, no derivative was found which displayed high potency in one assay but no activity in the other. This correlation further supports the conclusion that the inhibition of MetAP2 enzymatic activity mediates the anti-angiogenic activity of AGM-1470 and ovalicin.

Example 13
Screens for Agents that Inhibit MetAP2 and that are Anti-Angiogenic and/or Immunosuppressive This example illustrates methods for screening for agents that inhibit MetAP2 and that are anti-angiogenic and/or immunosuppressive.

(a) MetAP2 Inhibitors

A methionine aminopeptidase assay (Zuo et al., Mol. Gen. Genetics 246:247–253 (1995)) is set up in a multi-well plate (e.g., a 96 or 384-well plate) using recombinant human MetAP2 purified according to Li and Chang (Biochem. Biophys. Res. Commun. 227:152–159 (1996)). Test agents are introduced prior to the addition of the substrate (Met-Gly-Met-Met) to initiate the reaction. The presence of a MetAP2 inhibitor in a sample is detected by the lack of enzyme reaction.

Alternatively, the map1 yeast mutant (Li and Chang, PNAS 92:12357–12361 (1995)) is used to screen for new inhibitors. The yeast map1 mutant (lacks MetAP1) is cultured either in liquid YPD or solid YDP agar in the presence of a test agent. If the test agent is a MetAP2 inhibitor it is detected by the lack of yeast cell proliferation in the media.

(b) Anti-Angiogenic Agents

The MetAP2 inhibitors identified from (a) are tested to determine if they inhibit angiogenesis by testing their ability to inhibit endothelial cell proliferation (Antoine et al., Cancer Res. 54:2073–2076 (1994)), as described in Example 7. Those test agents that inhibit endothelial cell proliferation are anti-angiogenic agents.

(c) Immunosuppressive Agents

The MetAP2 inhibitors identified from (a) are tested to determine if they are immunosuppressive by testing them in a mixed lymphocyte reaction (MLR). A mouse mixed lymphocyte reaction is set up using as stimulator irradiated spleen cells isolated from C57/B6 mice and as responder spleen cells from Balb/c mice according to standard protocol (Coligan et al. (eds.), Current Protocols in Immunology, New York, N.Y., John Wiley and Sons (1991)). The test agents are dissolved in medium and added at the beginning of the MLR. Cell proliferation is measured using [$^3$H]-thymidine incorporation into the MLR culture. Those test agents that inhibit MLR are immunosuppressive agents.

Example 14
Synthesis of the Ovalicin Photoaffinity Label

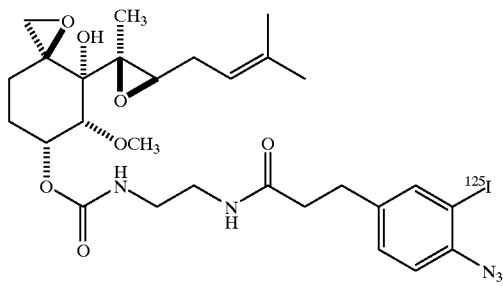

To a stirred solution of 4-hydroxyphenylpropionic acid N-hydroxysucuciamide (5.0 mg, 0.019 mmol) in 2 ml of EtOH was added carbamylovalicin-ethylamine (7.3 mg, 0.019 mmol) at 0° C. The reaction mixture was stirred for 0.5 hours at room temperture, then diluted with ethyl acetate and washed with saturated aqueous NaHCO$_3$ and brine. The organic phase was dried over anhydrous MgSO$_4$ and concentrated in vacuo. The residue was chromatographed on silica gel (MeOH/CHCl$_3$, 1:20 used as the eluent) to give 9.0 mg of product (80%) as colorless oil.

IR (neat) cm$^{-1}$: 3333, 2934, 1698, 1645, 1514, 1451, 1378, 1261, 1149, 1100, 828; $^1$H NMR (500 MHz, CDCl$_3$): 7.06 (2H, d, J=8.3 Hz), 6.79 (2H, d, J=8.3 Hz), 5.46–5.40 (2H, m), 5.19 (1H, t, J=7.3 Hz), 4.49 (1H, br. s), 3.67 (1H, d, J=3.3 Hz), 3.48 (3H, s), 3.26–3.05 (3H, series of m), 3.03 (1H, t, J=6.3 Hz), 2.99 (1H, d, J=4.4 Hz), 2.90 (2H, t, J=6.3 Hz), 2.56 (1H, d, J=4.4 Hz), 2.48–2.32 (5H, series of m), 2.20–2.10 (1H, m), 2.00–1.80 (2H, 2m), 1.75 (3H, s), 1.67 (3H, s), 1.65–1.58 (2H, m), 1.36 (3H, s), 1.03 (1H, 2H); MS(FAB) m/z: 556.6 (M+Na$^+$, 100).

Example 15
Synthesis of Biotin-Fumagillin

To a stirred solution of biotinsucuciamide (22 mg, 0.064 mmol) in 3 ml of the dried DMF was added carbamylfumagillol-decylamine (30 mg, 0.062 mmol) at 0° C. The reaction mixture was stirred for 0.5 hours at room temperture, then diluted with ethyl acetate and washed with saturated aqueous NaHCO$_3$ and brine. The organic phase was dried over anhydrous MgSO$_4$ and concentrated in vacuo. The residue was chromatographed on silica gel (MeOH/CHCl$_3$, 5:95 used as the eluent) to give 42 mg of product (96%) as colorless oil.

IR (neat) cm$^{-1}$: 3300, 3221, 2926, 2857, 1699, 1640, 1542, 1458, 1251, 1207, 1133, 1108, 926, 729; $^1$H NMR (500 MHz, CDCl$_3$): 6.35 (1H, s), 6.05 (t, 1H, J=5.1 Hz), 5.61 (1H, s), 5.44 (1H, s), 5.19 (1H, t, J=6.8 Hz), 4.99 (1H, t, J=5.1 Hz), 4.51 (1H, m), 4.30 (1H, m), 3.65–3.60 (1H, 2 m), 3.42 (3H, s), 3.20 (2H, q, J=6.6 Hz), 3.17–3.08 (3H, m), 2.95 (1H, d, J=4.4 Hz), 2.89 (1H, dd, J=12.7, 4.9 Hz), 2.72 (1H, d, J=12.7 Hz), 2.57–2.50 (2H, m), 2.38–2.30 (1H, m), 2.21–1.97 (4H, series of m), 1.92 (1H, d, J=11.2 Hz), 1.85–1.75 (1H, m), 1.73 (3H, s), 1.72–1.60 (3H, series of m), 1.64 (3H, s), 1.50–1.40 (6H, m), 1.33–1.22 (14H, m), 1.19 (3H, s), 1.04 (1H, d, J=12.7 Hz); MS(FAB) m/z: 729 (M+Na$^+$, 100).

The biotin-ovalicin conjugate was synthesized in a similar manner.

Those skilled in the art will be able to ascertain using no more than routine experimentation, many equivalents of the specific embodiments of the invention described herein. These and all other equivalents are intended to be encompassed by the following claims.

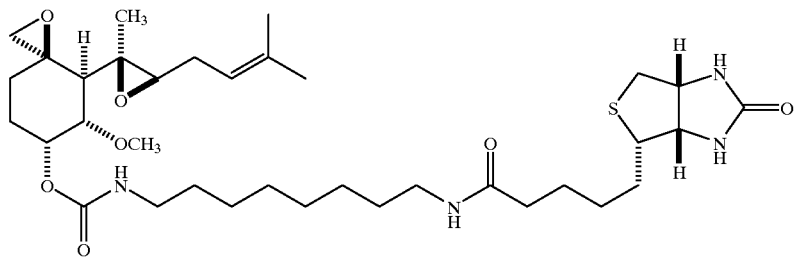

What is claimed is:
1. A compound of the formula:

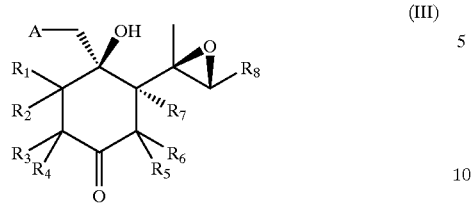

(III)

and pharmaceutically acceptable salts thereof,
wherein
A is a halogen, $N^+P_1P_2P_3X^-$ or $S^+P_1P_2X^-$, wherein $P_1$, $P_2$ and $P_3$ can be the same or different and are each an optionally substituted hydrocarbon or heterocyclic group and $X^-$ is a counter anion;

$R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is hydrogen; and $R_8$ is
(1) hydrogen or a substituted alkyl, allyl or alkyne group; or
(2) a substituted alkoxyl or thioalkoxyl group, or methylene or ethylene alkoxyl or thioalkoxyl group, wherein the methylene or ethylene can be optionally substituted;
(3) an aroyl group which can be optionally substituted with at least one substituent selected from the group consisting of alkyl, amino, alkylamino, dialkylamino, halogen, hydroxyl, lower alkoxyl, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or
(4) an aryl group which can be optionally substituted with at least one substituent selected from the group consisting of alkyl, amino, alkylamino, dialkylarnino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or
(5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or
(6) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or
(7) a benzenesulfonyl, methylsulfonyl or alkyl sufonyl group, with or without a methylene or ethylene substituent, or the corresponding amide or ester, which can be optionally substituted; or
(8) an alkoxycarbonyl or phenoxycarbonyl group with or without a methylene or ethylene substituent, which can be optionally substituted.

2. A compound of the formula:

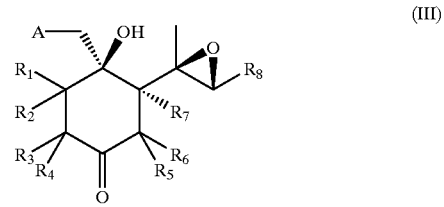

(III)

and pharmaceutically acceptable salts thereof,
wherein
A is $N^+P_1P_2P_3X^-$ or $S^+P_1P_2X^-$, wherein $P_1$, $P_2$ and $P_3$ can be the same or different and are each an optionally substituted hydrocarbon or heterocyclic group and $X^-$ is a counter anion;

$R_1$, $R_2$, $R_3$, $R_4$, $R_5$ and $R_6$ can be the same or different from each other and are hydrogen, alkyl, aryl, halogen, hydroxyl, alkoxy, carbamoyl, carbonyldioxyl, thiohydroxyl, amino, alkylamino, dialkylamino, ureido, lower alkoxy, a substituted alkanoyl group, a cyclic or aromatic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl and alkylthioether;

$R_7$ is a hydroxy group; and $R_8$ is
(1) hydrogen or a substituted alkyl, allyl or alkyne group; or
(2) a substituted alkoxyl or thioalkoxyl group, or methylene or ethylene alkoxyl or thioalkoxyl group, wherein the methylene or ethylene can be optionally substituted;
(3) an aroyl group which can be optionally substituted with at least one substituent selected from the group consisting of alkyl, amino, alkylamino, dialkylamino, halogen, hydroxyl, lower alkoxyl, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (4) an aryl group which can be optionally substituted with at least one substituent selected from the group consisting of alkyl, amino, alkylamino, dialkylamino, halogen, hydroxyl, lower alkoxy, cyano, amido, carbamoyl, thiocarbamoyl, carbonyldioxyl, carboxylic acid, carboxyl ester, carboxyl salt, alkyl or dialkylcarbamoyl, substituted ureido, vinyl, cyclic or aromatic cyclic groups which can be optionally substituted, or a heterocyclic or aromatic heterocyclic group which can be optionally substituted; or (5) an amino, alkylamino, dialkylamino, halogen, hydroxyl, cyano, amido, carbamoyl, thiocarbamoyl, carbonyldioxyl, carboxyl, alkyl, dialkylcarbamoyl, ureido, vinyl, cyclic or aromatic cyclic groups which can be optionally substituted, a heterocyclic or aromatic heterocyclic group which can be optionally substituted, carboxylic acid, carboxyl ester, carboxyl salt; or (6) 2-methyl-1-propenyl or an isobutyl group which can be optionally substituted with hydroxyl, carbamoyl, carbonyldioxyl, thiohydroxyl, amino, alkylamino, dialkylamino, ureido, alky, lower alkoxy, a substituted alkanoyl group, a cyclic or aromatic cyclic group which can be optionally substituted, a heterocyclic or aromatic heterocyclic group which can be optionally substituted, a substituted aryl or aroyl group having at least one substituent selected from the group consisting of alkyl, amino, halogen, hydroxyl, lower alkoxy, cyano, amide, carbamoyl, carboxylic acid, carboxyl ester, carboxyl salt, hydroxyl or alkylthioether; or (7) a benzenesulfonyl, methylsulfonyl or alkyl sufonyl group, with or without a methylene or ethylene substituent, or the corresponding amide or ester, which can be optionally substituted; or (8) an alkoxycarbonyl or phenoxycarbonyl group with or without a methylene or ethylene substituent, which can be optionally substituted.

3. A pharmaceutical composition for treating abnormal angiogenesis in an animal, comprising:

a therapeutically effective amount of an agent wherein said agent is selected from the compounds of claim 1 or 2, said agent being capable of altering an aspect of MetAP2 metabolism or structure in said animal so as to result in treatment of said abnormal angiogenesis; and a pharmaceutically acceptable carrier.

4. A pharmaceutical composition for treating an immune reaction which results in pathology in an animal, comprising:

a therapeutically effective amount of an agent wherein said agent is selected from compounds of claim 1 or 2, said agent being capable of altering an aspect of MetAP2 metabolism or structure in said animal so as to result in treatment of said immune reaction; and a pharmaceutically acceptable carrier.

\* \* \* \* \*

SEQUENCE LISTING

<160> NUMBER OF SEQ ID NOS: 4

<210> SEQ ID NO 1
<211> LENGTH: 478
<212> TYPE: PRT
<213> ORGANISM: Mus musculus

<400> SEQUENCE: 1

Met Ala Gly Val Glu Gln Ala Ala Ser Phe Gly Gly His Leu Asn Gly
 1               5                  10                  15

Asp Leu Asp Pro Asp Asp Arg Glu Glu Gly Thr Ser Ser Thr Ala Glu
             20                  25                  30

Glu Ala Ala Lys Lys Arg Arg Lys Lys Lys Gly Lys Gly Ala
         35                  40                  45

Val Ser Ala Val Gln Gln Glu Leu Asp Lys Glu Ser Gly Ala Leu Val
     50                  55                  60

Asp Glu Val Ala Lys Gln Leu Glu Ser Gln Ala Leu Glu Glu Lys Glu
 65                  70                  75                  80

Arg Asp Asp Asp Glu Asp Gly Asp Gly Asp Ala Asp Gly Ala Thr
                 85                  90                  95

Gly Lys Lys Lys Lys Lys Lys Lys Arg Gly Pro Lys Val Gln
                100                 105                 110

Thr Asp Pro Pro Ser Val Pro Ile Cys Asp Leu Tyr Pro Asn Gly Val
            115                 120                 125

Phe Pro Lys Gly Gln Glu Cys Glu Tyr Pro Pro Thr Gln Asp Gly Arg
        130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
                165                 170                 175

Arg Gln Val Arg Lys Tyr Val Met Ser Trp Ile Lys Pro Gly Met Thr
            180                 185                 190

Met Ile Glu Ile Cys Glu Lys Leu Glu Asp Cys Ser Arg Lys Leu Ile
        195                 200                 205

Lys Glu Asn Gly Leu Asn Ala Gly Leu Ala Phe Pro Thr Gly Cys Ser
    210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
            260                 265                 270

Tyr Asp Ile Leu Leu Thr Ala Val Lys Asp Ala Thr Asn Thr Gly Ile
        275                 280                 285

Lys Cys Ala Gly Ile Asp Val Arg Leu Cys Asp Val Gly Glu Ala Ile
    290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Pro Tyr
                325                 330                 335

Arg Ile His Ala Gly Lys Thr Val Pro Ile Val Lys Gly Gly Glu Ala
            340                 345                 350

Thr Arg Met Glu Glu Gly Glu Val Tyr Ala Ile Glu Thr Phe Gly Ser

```
            355                 360                 365
Thr Gly Lys Gly Val Val His Asp Asp Met Glu Cys Ser His Tyr Met
        370                 375                 380
Lys Asn Phe Asp Val Gly His Val Pro Ile Arg Leu Pro Arg Thr Lys
385                 390                 395                 400
His Leu Leu Asn Val Ile Asn Glu Asn Phe Gly Thr Leu Ala Phe Cys
                405                 410                 415
Arg Arg Trp Leu Asp Arg Leu Gly Glu Ser Lys Tyr Leu Met Ala Leu
            420                 425                 430
Lys Asn Leu Cys Asp Leu Gly Ile Val Asp Pro Tyr Pro Pro Leu Cys
            435                 440                 445
Asp Ile Lys Gly Ser Tyr Thr Ala Gln Phe Glu His Thr Ile Leu Leu
        450                 455                 460
Arg Pro Thr Cys Lys Glu Val Val Ser Arg Gly Asp Asp Tyr
465                 470                 475

<210> SEQ ID NO 2
<211> LENGTH: 478
<212> TYPE: PRT
<213> ORGANISM: Rattus norvegicus

<400> SEQUENCE: 2

Met Ala Gly Val Glu Glu Ala Ser Ser Phe Gly Gly His Leu Asn Arg
 1               5                  10                  15
Asp Leu Asp Pro Asp Asp Arg Glu Glu Gly Thr Ser Ser Thr Ala Glu
            20                  25                  30
Glu Ala Ala Lys Lys Lys Arg Arg Lys Lys Lys Gly Lys Gly Ala
        35                  40                  45
Val Ser Ala Gly Gln Gln Glu Leu Asp Lys Glu Ser Gly Thr Ser Val
    50                  55                  60
Asp Glu Val Ala Lys Gln Leu Glu Arg Gln Ala Leu Glu Glu Lys Glu
65                  70                  75                  80
Lys Asp Asp Asp Glu Asp Gly Asp Gly Asp Gly Asp Gly Ala Ala
                85                  90                  95
Gly Lys Lys Lys Lys Lys Lys Lys Arg Gly Pro Arg Val Gln
            100                 105                 110
Thr Asp Pro Pro Ser Val Pro Ile Cys Asp Leu Tyr Pro Asn Gly Val
        115                 120                 125
Phe Pro Lys Gly Gln Glu Cys Glu Tyr Pro Pro Thr Gln Asp Gly Arg
    130                 135                 140
Thr Ala Ala Trp Arg Thr Thr Ser Glu Glu Lys Lys Ala Leu Asp Gln
145                 150                 155                 160
Ala Ser Glu Glu Ile Trp Asn Asp Phe Arg Glu Ala Ala Glu Ala His
                165                 170                 175
Arg Gln Val Arg Lys Tyr Val Met Ser Trp Ile Lys Pro Gly Met Thr
            180                 185                 190
Met Ile Glu Ile Cys Glu Lys Leu Glu Asp Cys Ser Arg Lys Leu Ile
        195                 200                 205
Lys Glu Asn Gly Leu Asn Ala Gly Leu Ala Phe Pro Thr Gly Cys Ser
    210                 215                 220
Leu Asn Asn Cys Ala Ala His Tyr Thr Pro Asn Ala Gly Asp Thr Thr
225                 230                 235                 240
Val Leu Gln Tyr Asp Asp Ile Cys Lys Ile Asp Phe Gly Thr His Ile
                245                 250                 255
```

-continued

```
Ser Gly Arg Ile Ile Asp Cys Ala Phe Thr Val Thr Phe Asn Pro Lys
            260                 265                 270

Tyr Asp Ile Leu Leu Lys Ala Val Lys Asp Ala Thr Asn Thr Gly Ile
            275                 280                 285

Lys Cys Ala Gly Ile Asp Val Arg Leu Cys Asp Val Gly Glu Ala Ile
            290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Pro Tyr
                325                 330                 335

Arg Ile His Ala Gly Lys Thr Val Pro Ile Val Lys Gly Gly Glu Ala
            340                 345                 350

Thr Arg Met Glu Glu Gly Glu Val Tyr Ala Ile Glu Thr Phe Gly Ser
            355                 360                 365

Thr Gly Lys Gly Val Val His Asp Asp Met Glu Cys Ser His Tyr Met
            370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
                405                 410                 415

Arg Arg Trp Leu Asp Arg Leu Gly Glu Ser Lys Tyr Leu Met Ala Leu
            420                 425                 430

Lys Asn Leu Cys Asp Leu Gly Ile Val Asp Pro Tyr Pro Pro Leu Cys
            435                 440                 445

Asp Ile Lys Gly Ser Tyr Thr Ala Gln Phe Glu His Thr Ile Leu Leu
            450                 455                 460

Arg Pro Thr Cys Lys Glu Val Val Ser Arg Gly Asp Asp Tyr
465                 470                 475

<210> SEQ ID NO 3
<211> LENGTH: 478
<212> TYPE: PRT
<213> ORGANISM: Homo sapiens

<400> SEQUENCE: 3

Met Ala Gly Val Glu Glu Val Ala Ala Ser Gly Ser His Leu Asn Gly
  1               5                  10                  15

Asp Leu Asp Pro Asp Asp Arg Glu Glu Gly Ala Ala Ser Thr Ala Glu
                 20                  25                  30

Glu Ala Ala Lys Lys Lys Arg Arg Lys Lys Lys Ser Lys Gly Pro
             35                  40                  45

Ser Ala Ala Gly Glu Gln Glu Pro Asp Lys Glu Ser Gly Ala Ser Val
 50                  55                  60

Asp Glu Val Ala Arg Gln Leu Glu Arg Ser Ala Leu Glu Asp Lys Glu
 65                  70                  75                  80

Arg Asp Glu Asp Asp Glu Asp Gly Asp Gly Asp Gly Asp Gly Ala Thr
                 85                  90                  95

Gly Lys Lys Lys Lys Lys Lys Lys Lys Arg Gly Pro Lys Val Gln
            100                 105                 110

Thr Asp Pro Pro Ser Val Pro Ile Cys Asp Leu Tyr Pro Asn Gly Val
            115                 120                 125

Phe Pro Lys Gly Gln Glu Cys Glu Tyr Pro Pro Thr Gln Asp Gly Arg
            130                 135                 140

Thr Ala Ala Trp Arg Thr Thr Ser Glu Glu Lys Lys Ala Leu Asp Gln
145                 150                 155                 160
```

Ala Ser Glu Glu Ile Trp Asn Asp Phe Arg Glu Ala Glu Ala His
            165                 170                 175

Arg Gln Val Arg Lys Tyr Val Met Ser Trp Ile Lys Pro Gly Met Thr
        180                 185                 190

Met Ile Glu Ile Cys Glu Lys Leu Glu Asp Cys Ser Arg Lys Leu Ile
    195                 200                 205

Lys Glu Asn Gly Leu Asn Ala Gly Leu Ala Phe Pro Thr Gly Cys Ser
210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
            245                 250                 255

Ser Gly Arg Ile Ile Asp Cys Ala Phe Thr Val Thr Phe Asn Pro Lys
        260                 265                 270

Tyr Asp Thr Leu Leu Lys Ala Val Lys Asp Ala Thr Asn Thr Gly Ile
    275                 280                 285

Lys Cys Ala Gly Ile Asp Val Arg Leu Cys Asp Val Gly Glu Ala Ile
290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Gln Tyr
            325                 330                 335

Arg Ile His Ala Gly Lys Thr Val Pro Ile Val Lys Gly Gly Glu Ala
        340                 345                 350

Thr Arg Met Glu Glu Gly Glu Val Tyr Ala Ile Glu Thr Phe Gly Ser
    355                 360                 365

Thr Gly Lys Gly Val Val His Asp Asp Met Glu Cys Ser His Tyr Met
370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
            405                 410                 415

Arg Arg Trp Leu Asp Arg Leu Gly Glu Ser Lys Tyr Leu Met Ala Leu
        420                 425                 430

Lys Asn Leu Cys Asp Leu Gly Ile Val Asp Pro Tyr Pro Pro Leu Cys
    435                 440                 445

Asp Ile Lys Gly Ser Tyr Thr Ala Gln Phe Glu His Thr Ile Leu Leu
450                 455                 460

Arg Pro Thr Cys Lys Glu Val Val Ser Arg Gly Asp Tyr
465                 470                 475

<210> SEQ ID NO 4
<211> LENGTH: 421
<212> TYPE: PRT
<213> ORGANISM: Saccharomyces cerevisiae

<400> SEQUENCE: 4

Met Thr Asp Ala Glu Ile Glu Asn Ser Pro Ala Ser Asp Leu Lys Glu
  1               5                  10                  15

Leu Asn Leu Glu Asn Glu Gly Val Glu Gln Gln Asp Gln Ala Lys Ala

-continued

```
                 20                  25                  30
Asp Glu Ser Asp Pro Val Glu Ser Lys Lys Lys Asn Lys Lys Lys
             35                  40                  45
Lys Lys Lys Lys Ser Asn Val Lys Lys Ile Glu Leu Leu Phe Pro Asp
         50                  55                  60
Gly Lys Tyr Pro Glu Gly Ala Trp Met Asp Tyr His Gln Asp Phe Asn
 65                  70                  75                  80
Leu Gln Arg Thr Thr Asp Glu Glu Ser Arg Tyr Leu Lys Arg Asp Leu
                 85                  90                  95
Glu Arg Ala Glu His Trp Asn Asp Val Arg Lys Gly Ala Glu Ile His
             100                 105                 110
Arg Arg Val Arg Arg Ala Ile Lys Asp Arg Ile Val Pro Gly Met Lys
         115                 120                 125
Leu Met Asp Ile Ala Asp Met Ile Glu Asn Thr Thr Arg Lys Tyr Thr
     130                 135                 140
Gly Ala Glu Asn Leu Leu Ala Met Glu Asp Pro Lys Ser Gln Gly Ile
145                 150                 155                 160
Gly Phe Pro Thr Gly Leu Ser Leu Asn His Cys Ala Ala His Phe Thr
                 165                 170                 175
Pro Asn Ala Gly Asp Lys Thr Val Leu Lys Tyr Glu Asp Val Met Lys
             180                 185                 190
Val Asp Tyr Gly Val Gln Val Asn Gly Asn Ile Ile Asp Ser Ala Phe
         195                 200                 205
Thr Val Ser Phe Asp Pro Gln Tyr Asp Asn Leu Leu Ala Ala Val Lys
     210                 215                 220
Asp Ala Thr Tyr Thr Gly Ile Lys Glu Ala Gly Ile Asp Val Arg Leu
225                 230                 235                 240
Thr Asp Ile Gly Glu Ala Ile Gln Glu Val Met Glu Ser Tyr Glu Val
                 245                 250                 255
Glu Ile Asn Gly Glu Thr Tyr Gln Val Lys Pro Cys Arg Asn Leu Cys
             260                 265                 270
Gly His Ser Ile Ala Pro Tyr Arg Ile His Gly Gly Lys Ser Val Pro
         275                 280                 285
Ile Val Lys Asn Gly Asp Thr Thr Lys Met Glu Glu Gly Glu His Phe
     290                 295                 300
Ala Ile Glu Thr Phe Gly Ser Thr Gly Arg Gly Tyr Val Thr Ala Gly
305                 310                 315                 320
Gly Glu Val Ser His Tyr Ala Arg Ser Ala Glu Asp His Gln Val Met
                 325                 330                 335
Pro Thr Leu Asp Ser Ala Lys Asn Leu Leu Lys Thr Ile Asp Arg Asn
             340                 345                 350
Phe Gly Thr Leu Pro Phe Cys Arg Arg Tyr Leu Asp Arg Leu Gly Gln
         355                 360                 365
Glu Lys Tyr Leu Phe Ala Leu Asn Asn Leu Val Arg His Gly Leu Val
     370                 375                 380
Gln Asp Tyr Pro Pro Leu Asn Asp Ile Pro Gly Ser Tyr Thr Ala Gln
385                 390                 395                 400
Phe Glu His Thr Ile Leu Leu His Ala His Lys Lys Glu Val Val Ser
                 405                 410                 415
Lys Gly Asp Asp Tyr
             420
```